United States Patent
Obata et al.

(10) Patent No.: US 7,977,020 B2
(45) Date of Patent: Jul. 12, 2011

(54) ELECTROPHOTOGRAPHIC PHOTORECEPTOR CONTAINING ENAMINE COMPOUND, IMAGE FORMATION APPARATUS PROVIDED WITH THE SAME, ENAMINE COMPOUND AND METHOD FOR PRODUCING THE SAME

(75) Inventors: Takatsugu Obata, Nara (JP); Akihiro Kondoh, Nara (JP)

(73) Assignee: Sharp Kabushiki Kaisha, Osaka (JP)

( * ) Notice: Subject to any disclaimer, the term of this patent is extended or adjusted under 35 U.S.C. 154(b) by 585 days.

(21) Appl. No.: 12/081,974

(22) Filed: Apr. 24, 2008

(65) Prior Publication Data
US 2008/0286671 A1    Nov. 20, 2008

(30) Foreign Application Priority Data

May 10, 2007  (JP) ................................. 2007-126000

(51) Int. Cl.
*G03G 15/02* (2006.01)

(52) U.S. Cl. .................. 430/58.35; 430/58.65; 399/119; 399/174

(58) Field of Classification Search ............... 430/58.35, 430/58.65; 399/119, 174
See application file for complete search history.

(56) References Cited

U.S. PATENT DOCUMENTS

| | | | |
|---|---|---|---|
| 4,952,470 A | 8/1990 | Tamaki et al. | |
| 5,102,759 A | 4/1992 | Fuse et al. | |
| 5,130,222 A | 7/1992 | Otsuka et al. | |
| 2004/0101770 A1* | 5/2004 | Obata et al. | 430/58.85 |
| 2005/0164107 A1* | 7/2005 | Toriyama et al. | 430/73 |
| 2005/0232657 A1* | 10/2005 | Fujii et al. | 399/159 |
| 2006/0204871 A1* | 9/2006 | Kondoh et al. | 430/58.85 |
| 2006/0210895 A1* | 9/2006 | Obata et al. | 430/72 |
| 2006/0222979 A1* | 10/2006 | Ishida et al. | 430/72 |
| 2007/0077506 A1* | 4/2007 | Kihara et al. | 430/58.35 |

FOREIGN PATENT DOCUMENTS

| | | |
|---|---|---|
| JP | 63-004238 | 1/1988 |
| JP | 63-018355 | 1/1988 |
| JP | 63-216055 | 9/1988 |
| JP | 03-172852 | 7/1991 |
| JP | 05-158258 | 6/1993 |
| JP | 62-105151 | 5/1997 |
| JP | 10-069107 | 3/1998 |

OTHER PUBLICATIONS

Abstract of Highly chemoselective formation of aldehyde enanines under very mild reaction conditions, Journal of Organic Chemistry (2006), 7481-7484, Belanger et al, Aug. 24, 2006.*
Bélanger et al, "Highly Chemoselective Formation of Aldehyde Enamines Under Very Mild Reaction Conditions", J. Org. Chem., vol. 71, No. 19, 2006, pp. 7481-7484.

* cited by examiner

*Primary Examiner* — Hoa V Le
(74) *Attorney, Agent, or Firm* — Nixon & Vanderhye P.C.

(57) ABSTRACT

An electrophotographic photoreceptor comprising laminating a monolayer type photosensitive layer containing a charge generation material and a charge transport material or a laminate type photosensitive layer obtained by laminating a charge generation layer containing a charge generation material and a charge transport layer containing a charge transport material in this order, on a conductive support, wherein the charge transport layer of the monolayer type photosensitive layer or laminate type photosensitive layer contains an enamine compound represented by the following formula (1).

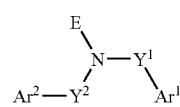

(1)

8 Claims, 4 Drawing Sheets

ELECTROPHOTOGRAPHIC PHOTORECEPTOR CONTAINING ENAMINE COMPOUND, IMAGE FORMATION APPARATUS PROVIDED WITH THE SAME, ENAMINE COMPOUND AND METHOD FOR PRODUCING THE SAME

CROSS-REFERENCE TO RELATED APPLICATIONS

This application is related to Japanese Patent Application No. 2007-126000 filed on May 10, 2007 whose priority is claimed under 35 USC §119, the disclosure of which is incorporated by reference in its entirety.

BACKGROUND OF THE INVENTION

1. Field of the Invention

The present invention relates to an electro-photographic photoreceptor containing an enamine compound capable of efficiently preventing image defects caused by oxidizing gas such as ozone and NOx, to an image formation apparatus provided with the electro-photographic photoreceptor, to an enamine compound and to a method for producing the enamine compound.

2. Description of the Related Art

Many electrophotographic system image formation apparatus (hereinafter also referred to as "electrophotographic device") utilizing electrophotographic technologies to form an image are used for copying machines, printers, facsimile machines and the like.

In electrophotographic devices, an image is formed through an electrophotographic process mentioned below. First, the photosensitive layer of the electrophotographic photoreceptor (hereinafter also called "photoreceptor") provided in the devices is charged and then exposed to light to form an electrostatic latent image. The formed electrostatic latent image is developed to form a toner image. Then, the formed toner image is transferred and fixed to a transfer receiving material such as recording paper to form a desired image on the transfer receiving material.

The electrophotographic technologies are currently utilized not only in the fields of copying machines but also in the fields of printing precursors, slide films, microfilms and the like, in which silver salt photo technologies have been conventionally utilized. These technologies are also applied to high-speed printers using, as its light source, a laser, light emitting diode (abbreviation: LED), cathode ray tube (abbreviation: CRT) and the like. Along with a spread of the range of applications of electrophotographic technologies, the requirements in the photoreceptors are becoming highly advanced and widely spread.

As the photoreceptor, widely used are inorganic photoreceptors which are provided with a photosensitive layer containing, as its major component, inorganic photoconductive materials such as selen, zinc oxide or cadmium sulfide.

The inorganic photoreceptor has fundamental characteristics required of photoreceptors to some extent. However, the inorganic photoreceptor has the drawback such that it has a difficulty in forming a film of the photosensitive layer, is deteriorated in plasticity and has high production cost. Also, the inorganic photoconductive materials are highly toxic in usual and are therefore largely limited in its production and handling.

As mentioned above, since these inorganic photoconductive materials and inorganic photoreceptors using these inorganic photoconductive materials have many drawbacks, the progress of research and development of organic photoconductive materials have been made.

In recent years, the organic photoconductive materials have been widely studied and developed. The organic photoconductive materials not only are utilized for electrostatic recording devices but also have become used in applications of sensor devices, organic electro luminescent (abbreviation: EL) devices and the like.

The organic photoreceptor using the organic photoconductive material have the advantage that the photosensitive layer is well formed as a film, is superior in flexibility, is light-weighted and has high transparency and therefore, a photoreceptor having high sensitivity for light in a wide wavelength range by an appropriate sensitizing method can be easily designed. Therefore, the organic photoreceptors are being developed as a leading photoreceptor day by day.

Though the organic photoreceptors have the drawbacks that they are deteriorated in sensitivity and durability in the early stages, these drawbacks have been significantly improved by the development of function separating type photoreceptors in which the charge generation function and charge transport function are shared by separate materials. Moreover, this function separating type photoreceptor has the advantage that the material constituting the photosensitive layer can be selected from a wide range of materials, so that photoreceptors having desired characteristics can be manufactured relatively easily in addition to the above advantage specific to the organic photoreceptors.

As the structure of such an organic photoreceptor, various structures have been proposed, these structures including a single layer structure in which a charge generation material and a charge transport material (also called "charge transport material" are both dispersed in a binder, which is then applied to a support and a laminate structure or reverse double layer type structure in which a charge generation layer obtained by dispersing a charge generation material in a binder and a charge transport layer obtained by dispersing a charge transport material in a binder resin are formed in this order or reverse order on a support. Among these structures, a functional separation type photoreceptor in which a charge transport layer is laminated on a charge generation layer is superior in electrophotographic characteristics and durability. Therefore, the photoreceptor characteristics can be variously designed due to its high degree of freedom of material selection, and are hence widely put to practical use.

As the charge generation material to be used in these function separation type photoreceptors, studies have been made as to various materials such as a phthalocyanine pigment, squalilium dye, azo pigment, perylene pigment, polycyclic quinine pigment, cyanine dye, squalenic acid dye and pyrylium salt type dye, and a variety of materials having high light fastness and high charge generation ability have been proposed.

Also, as the charge transport material, various compounds are known which include pyrazoline compounds, hydrazone compounds, triphenylamine compounds, stilbene compounds and enamine compounds.

Various performances such as a high-speed operation, durability and sensitive stability are demanded of photoreceptors having the structures that have been proposed or investigated. With regard to the characteristics of the photoreceptor, high sensitization that copes with a high-speed operation and an improvement in durability (=long life) which is made by an improvement in abrasive resistance and sensitive stabilization are required at the same time corresponding to a reverse developing system electrophotographic device such as a laser printer. In addition, higher image reliability and stability in repeated use are required of photoreceptors such as a laser printer.

However, it has been regarded as one large drawback of these photoreceptors that these photoreceptors are generally more deteriorated in durability than inorganic type photoreceptors. The durability is roughly divided into a kind of durability of photographic properties such as sensitivity, residual potential, charge ability and image fogs, and mechanical durability of, for example, abrasion and scratches of the surface of the photoreceptor caused by friction. The primary cause of a deterioration in durability of the photographic properties are known to be ozone, $NO_x$ (nitrogen oxides) and a deterioration caused by irradiation with light in a charge transport material contained in the surface layer of the photoreceptor. In the current circumstance, many charge transport materials constituted of various skeletons and proposed variously are not said to be satisfactory though improved in durability.

Also, the photoreceptor is repeatedly used in a system. In the system, it is required for the photoreceptor to always exhibit constantly stable photographic characteristics. In the current circumstance, as to such stability and durability, no structure satisfied in these properties has not been obtained yet so far.

Specifically, the repeated use of the photoreceptor causes a reduction in potential, a rise in residual potential and a change in sensitivity, bringing about a deterioration in the quality of copies, with the result that the photoreceptor cannot stand to use. Though all of the causes of the deterioration are not clarified, some causes are considered.

It has been clarified that oxidizing gases, for example, ozone and nitrogen oxide and the like emitted from a corona discharge/charge device give remarkable damages to the photosensitive layer. These oxidizing gases chemically change materials in the photoreceptor to bring about various characteristic changes. These oxidizing gases bring about, for example, a reduction in charge potential, rise in residual potential and reduction in resolution caused by a reduction in surface resistance, with the result that image fogs such as white voids and black bands occur on an output image, which deteriorate the image quality significantly and hence shortens the life of the photoreceptor. For such a phenomenon, there have been made a proposal including such ideas that gas around the corona charger is efficiently exhausted and replaced to avoid direct influence of the gas on the photoreceptor and a proposal in which an antioxidant and a stabilizer are added to the photosensitive layer to prevent the deterioration of the photoreceptor.

For example, it is disclosed in the publication of Japanese Unexamined Patent Publication No. SHO 62-105151 that an antioxidant having a triazine ring and a hindered phenol skeleton is added to a photosensitive layer and it is also disclosed in the publication of Japanese Unexamined Patent Publication No. SHO 63-18355 that a specific hindered amine is added to a photosensitive layer. It is also disclosed in each publication of Japanese Unexamined Patent Publication Nos. SHO 63-4238, SHO 63-216055 and HEI 3-172852 that a trialkylamine and an aromatic amine are added to a photosensitive layer. It is also disclosed in the publication of Japanese Unexamined Patent Publication No. HEI 5-158258 that an amine dimer is added in a photosensitive layer. However, these measures are still unsatisfactory.

SUMMARY OF THE INVENTION

According to a first aspect of the present invention, there is provided a photoreceptor comprising laminating a monolayer type photosensitive layer containing a charge generation material and a charge transport material or a laminate type photosensitive layer obtained by laminating a charge generation layer containing a charge generation material and a charge transport layer containing a charge transport material in this order, on a conductive support, wherein the charge transport layer of the above monolayer type photosensitive layer or laminate type photosensitive layer contains an enamine compound represented by the following formula (1):

wherein $Ar^1$ and $Ar^2$, which may be the same or different, respectively represent an aryl group which may have a substituent, a cycloalkyl group which may have a substituent or a monovalent heterocyclic residue which may have a substituent;

$Y^1$ and $Y^2$, which may be the same or different, represent a straight or branched chain alkylene group which may have a substituent;

E represents an enamine group selected from the following formulae (i), (ii) and (iii):

wherein $Ar^3$, $Ar^4$, $Ar^5$ and $Ar^6$, which may be the same or different, respectively represent an aryl group which may have a substituent; $R^1$ represents an alkyl group which may have a substituent; $R^2$ represents a straight or branched chain alkylene group which may have a substituent, an oxygen atom or a sulfur atom.

Also, according to a second aspect of the present invention, there is provided an image formation apparatus comprising the above photoreceptor, a charge means for charging the above photoreceptor, an exposure means for exposing the above charged photoreceptor to light and a developing means for developing the electrostatic latent image formed by the exposure.

Further, according to a third aspect of the present invention, there is provided an enamine compound represented by the following structural formula:

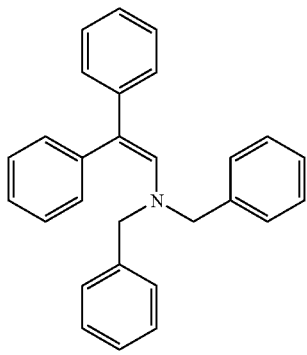

Also, according to a fourth aspect of the present invention, there is provided a method for producing an enamine compound, the method comprising bringing a dibenzylamine represented by the following structural formula:

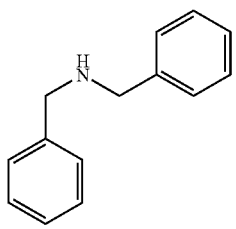

into contact with a diphenylacetaldehyde represented by the following structural formula:

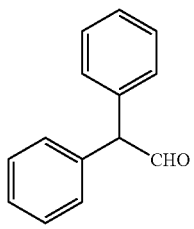

to undergo a dehydration condensation reaction in the presence of an acid catalyst to obtain the above enamine compound.

DESCRIPTION OF THE PREFERRED EMBODIMENTS

Figure 1:
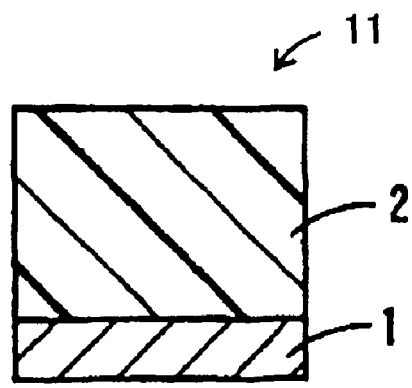
FIG. 1 is a schematic cross-sectional view showing the structure of an essential part of a monolayer type photoreceptor according to the present invention.

Specifically, the conventional technologies as mentioned above have failed to attain the effect of imparting sufficient resistance to ozone so far, and also, such practically unfavorable influences as to deteriorate photographic characteristics such as sensitivity and residual potential by addition of, for example, such an antioxidant still remain at present. Therefore, a proposal of a novel material that is improved in resistance to ozone and is free from harmful effects on electrophotographic characteristics is expected.

Accordingly, it is an object of the present invention to provide a novel enamine compound which can be used to provide a photoreceptor that is superior in ozone resistance effect and is free from harmful effects on other characteristics, a method for producing the enamine compound, a photoreceptor using the enamine compound and an image formation apparatus provided with the photoreceptor.

The inventors of the present invention have made earnest studies and as a result, found that, unexpectedly, a specified enamine compound is superior in ozone resistance, is also entirely free from harmful effects on photographic characteristics, and is very useful for a photoreceptor and for an image formation apparatus provided with the photoreceptor, to complete the present invention.

The photoreceptor of the present invention comprises laminating a monolayer type photosensitive layer containing a charge generation material and a charge transport material or a laminate type photosensitive layer obtained by laminating a charge generation layer containing a charge generation material and a charge transport layer containing a charge transport material in this order, on a conductive support, wherein the charge transport layer of the above monolayer type photosensitive layer or laminate type photosensitive layer contains an enamine compound represented by the above formula (1).

When the enamine compound of the present invention is blended in the photosensitive layer containing the organic photoconductive material, it produces a high ozone resistance effect and has no adverse influence on the photographic characteristics. This enamine compound is suitable as a compound used together with the organic photoconductive material.

Therefore, if the enamine compound of the present invention is compounded in, for example, a photosensitive layer of a photoreceptor, it is possible to provide a photoreceptor that has an ozone resistance effect and is superior in durability and environmental stability at the same time.

Also, the photoreceptor of the present invention can provide a high quality image due to that excellent ozone resistance effect even if it is used in a high-speed photographic process.

Thus, the use of the photoreceptor of the present invention ensures that a high quality image superior in ozone resistance effect even if it is used repeatedly for a long period of time.

Furthermore, the photoreceptor of the present invention contains the enamine compound of the present invention in the photosensitive layer and is therefore superior in ozone resistance effect and also in the photoreceptor resting memory phenomenon along with an increase in the life of the photoreceptor.

Therefore, in the image formation apparatus of the present invention, a high quality image free from any image defect can be formed stably in various environments for a long period of time.

Also, the photoreceptor of the present invention can provide a high quality image even in a high-speed electrophotographic process and therefore, the rate of image formation can be increased in the image formation apparatus of the present invention.

Moreover, according to the method for producing an enamine compound, the enamine compound can be obtained simply by a dehydration condensation reaction between a corresponding aldehyde compound and secondary amine compound in the presence of an acid catalyst.

Therefore, the compound obtained in the production method like this is quite free from the contamination with metal compounds arousing a fear as to harmful effects on photographic characteristics and can be obtained at high purity by a simple process without the necessity of extraction processes such as liquid separation.

Among enamine compounds represented by the formula (1), those represented by the following sub-formula (2) are preferable and those represented by the following sub-formula (3) are more preferable:

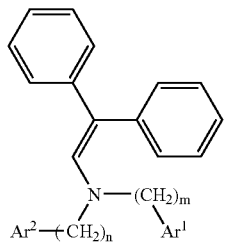

(2)

wherein $Ar^1$ and $Ar^2$ are the same as those defined in the formula (1); and n and m, which may be the same or different, respectively denote an integer from 1 to 3; and

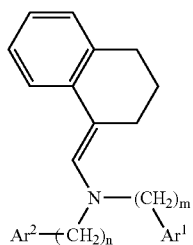

(3)

wherein $Ar^1$ and $Ar^2$ are the same as those defined in the formula (1); and n and m are the same as those defined in the sub-formula (2), in point of chemical stability of decomposition, change of properties and the like as chemical material; availability of raw material; easiness and yield level of the production; production cost, and the like.

The substituents in the formula (1), sub-formula (2) and sub-formula (3) will be explained.

Examples of the aryl group which may have a substituent in $Ar^1$ and $Ar^2$ include aryl groups which may be substituted with an alkyl group having 1 to 4 carbon atoms, an alkoxy group having 1 to 4 carbon atoms, a dialkylamino group having 2 to 6 carbon atoms or a halogen atom.

Specific examples of the aryl group include a phenyl group, tolyl group, xylyl group, methoxyphenyl group, methylmethoxyphenyl group, t-butylphenyl group, 4-diethylaminophenyl group, 4-chlorophenyl group, 4-fluorophenyl group, 4-trifluoromethylphenyl group, naphthyl group, methoxynaphthyl group, tetrahydronaphthanyl group and diisopropylaminophenyl group. Among these groups, a phenyl group, p-tolyl group, p-methoxyphenyl group, 1-naphthyl group, 2-tetrahydronaphthanyl group, 6-tetrahydronaphthanyl group and diisopropylaminophenyl group are particularly preferable.

Examples of the cycloalkyl group which may have a substituent in $Ar^1$ and $Ar^2$ include cycloalkyl groups which may be substituted with an alkyl group having 1 to 4 carbon atoms.

Specific examples of the cycloalkyl group include a cyclohexyl group, cyclopentyl group and 4,4-dimethylcyclohexyl group. Among these groups, a cyclohexyl group is preferable.

Examples of the monovalent heterocyclic residual group which may have a substituent in $Ar^1$ and $Ar^2$ include monovalent heterocyclic residual groups which may be substituted with an alkyl group having 1 to 4 carbon atoms.

Specific examples of the monovalent heterocyclic residual groups include a tetrahydrofuryl group, tetrahydropyranyl group, tetramethyltetrahydrofuryl group, furyl group, 4-methylfuryl group, benzofuryl group, isobenzofuryl group, benzothiophenyl group and thianaphthyl group. Among these groups, a furyl group and benzofuryl group are particularly preferable.

Examples of the straight or branched chain alkylene group which may have a substituent in $Y^1$ and $Y^2$ include alkylene groups which may be substituted with an alkyl group having 1 to 4 carbon atoms.

Specific examples of the alkylene group include a methylene group, ethylene group (dimethylene group), propylene group (trimethylene group) and 2,2-dimethylpropylene group. Among these groups, a methylene group and ethylene group are particularly preferable.

The enamine group E is an enamine group selected from the formulae (i), (ii) and (iii). The substituents of the enamine group will be explained.

Examples of the aryl group which may have a substituent in $Ar^3$, $Ar^4$, $Ar^5$ and $Ar^6$ include aryl groups which may be substituted with an alkyl group having 1 to 4 carbon atoms, an alkoxy group having 1 to 4 carbon atoms, a dialkylamino group having 2 to 6 carbon atoms or a halogen atom.

Specific examples of the aryl group include a phenyl group, tolyl group, xylyl group, methoxyphenyl group, methylmethoxyphenyl group, t-butylphenyl group, 4-diethylaminophenyl group, 4-chlorophenyl group, 4-fluorophenyl group, naphthyl group and methoxynaphthyl group. Among these groups, a phenyl group, p-tolyl group, p-chlorophenyl group and 2-naphthyl group are particularly preferable.

Examples of the alkyl group which may have a substituent in $R^1$ include alkyl groups having 1 to 4 carbon atoms such as a methyl group, ethyl group, propyl group, isopropyl group, butyl group, isobutyl group (1-methylpropyl group) and trifluoromethyl group. Among these groups, a methyl group, isobutyl group and trifluoromethyl group are particularly preferable.

Examples of the straight or branched chain alkylene group which may have a substituent in $R^2$ include alkylene groups which may be substituted with an alkyl group having 1 to 4 carbon atoms.

Specific examples of the alkylene group include a methylene group, ethylene group (dimethylene group), propylene group (trimethylene group), 2,2-dimethylpropylene group and ethyleneoxy group. Among these groups, an ethylene group, propylene group and ethyleneoxy group are particularly preferable.

E is preferably a group represented by the formula (i) in which $Ar^3$ and $Ar^4$ are respectively a phenyl group such as those represented by the sub-formula (2) or a group represented by the formula (iii) in which $Ar^6$ and $R^2$ are a phenyl group and a propylene group respectively such as those represented by the sub-formula (3).

Specific examples of the enamine compound represented by the formula (1) according to the present invention will be given below. Among these examples, the exemplified compounds Nos. 1, 2, 3, 7, 12, 17 and 24 are preferable and the exemplified compound No. 1 is particularly preferable.

exemplified compound No. 1

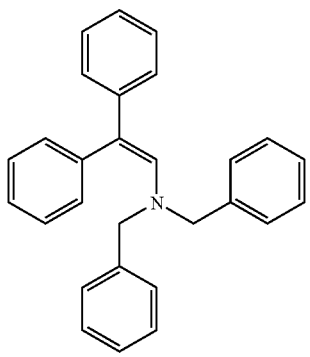

exemplified compound No. 2

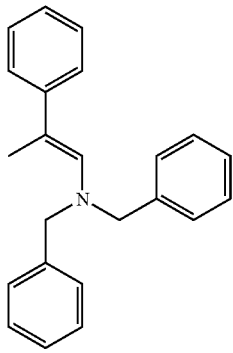

exemplified compound No. 3

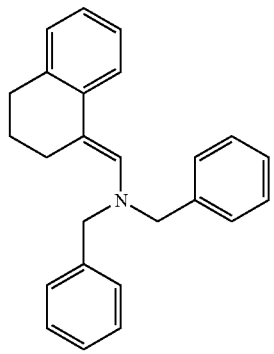

exemplified compound No. 4

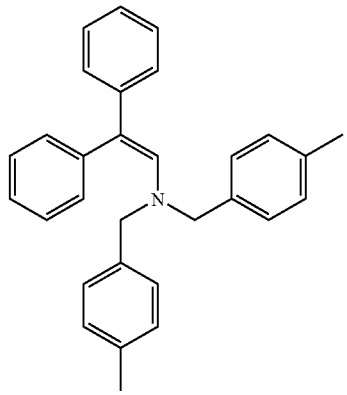

exemplified compound No. 5

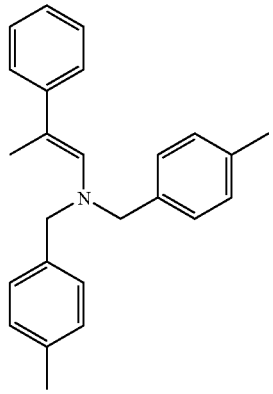

exemplified compound No. 6

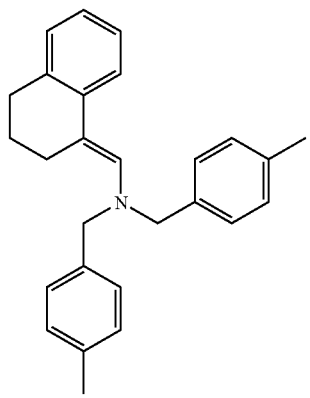

exemplified compound No. 7
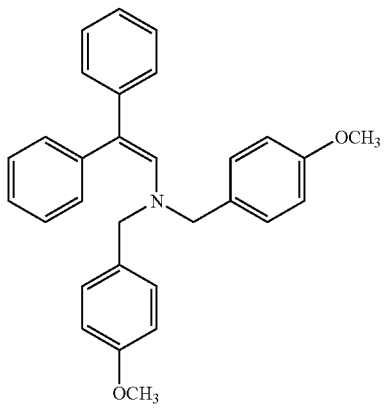
exemplified compound No. 8
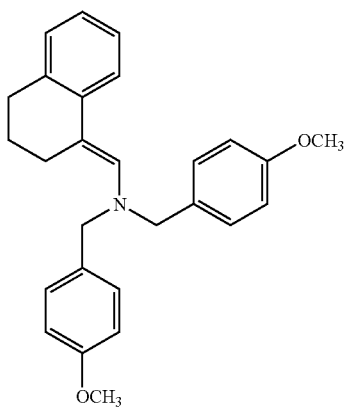
exemplified compound No. 9
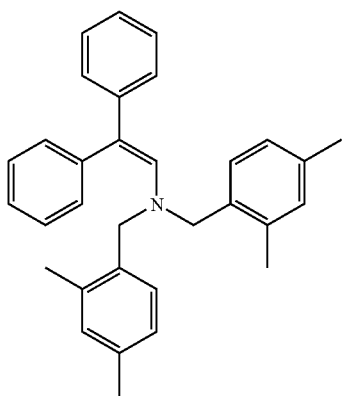
exemplified compound No. 10
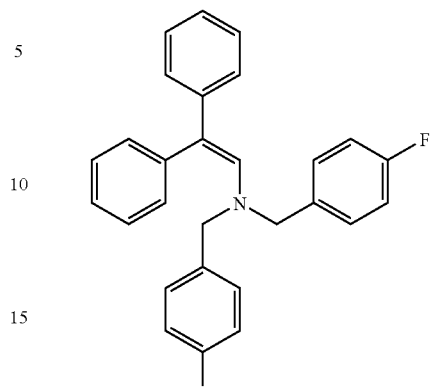
exemplified compound No. 11
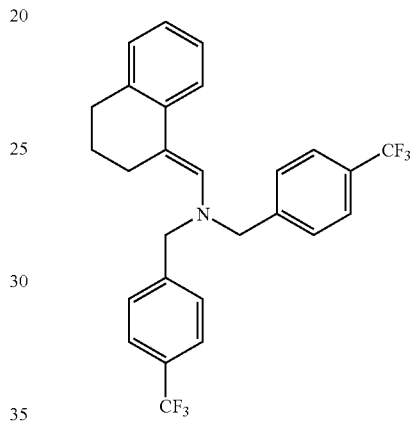
exemplified compound No. 12
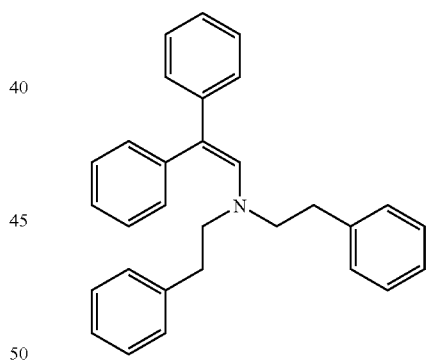
exemplified compound No. 13
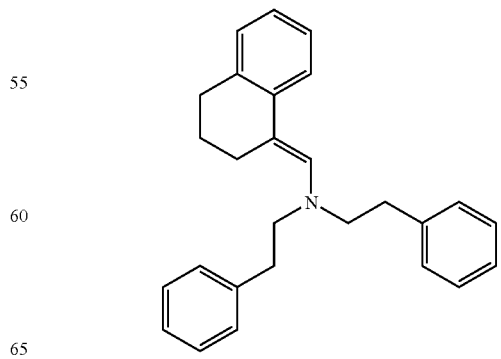

exemplified compound No. 14
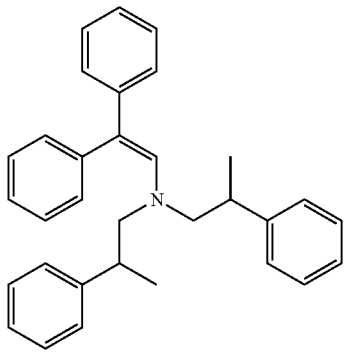
exemplified compound No. 15
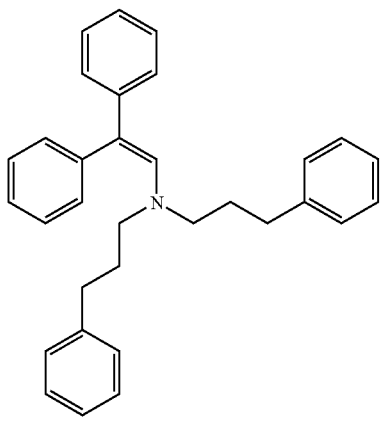
exemplified compound No. 16
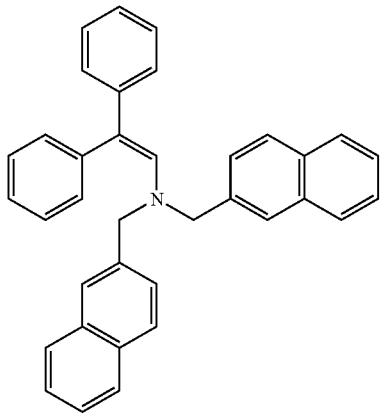
exemplified compound No. 17
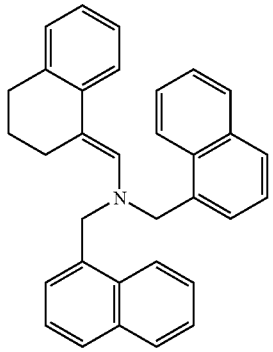
exemplified compound No. 18
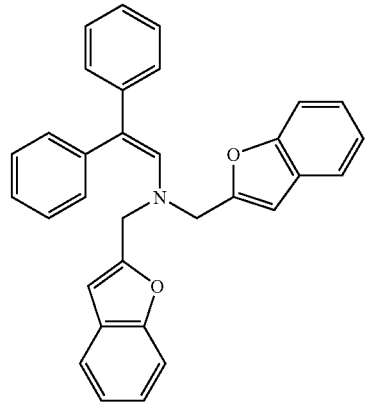
exemplified compound No. 19
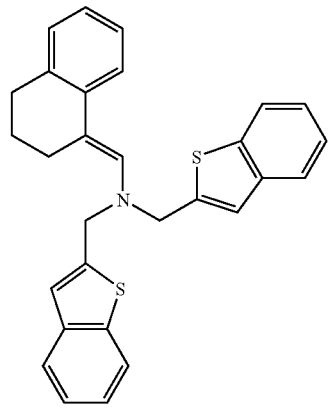
exemplified compound No. 20
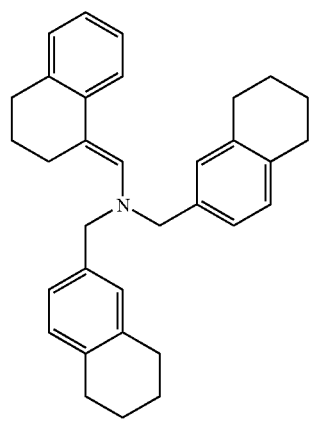
exemplified compound No. 21
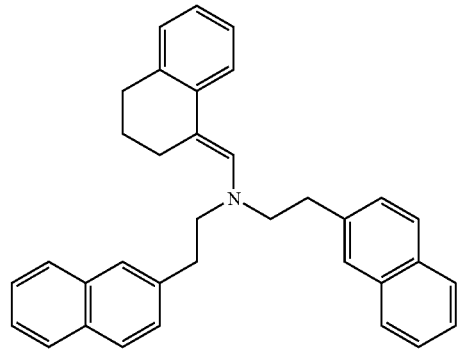

exemplified compound No. 22
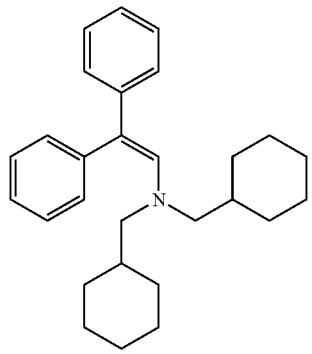
exemplified compound No. 23
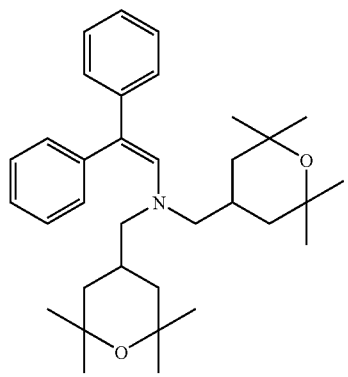
exemplified compound No. 24
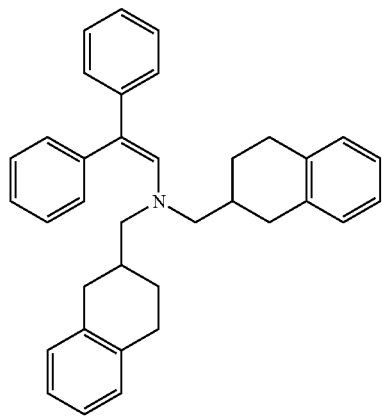
exemplified compound No. 25
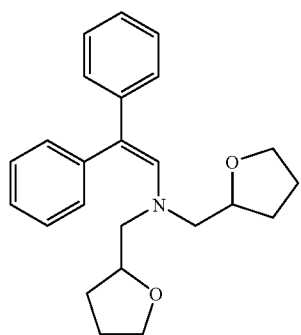
exemplified compound 26
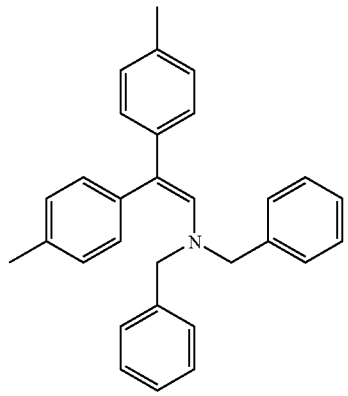
exemplified compound No. 27
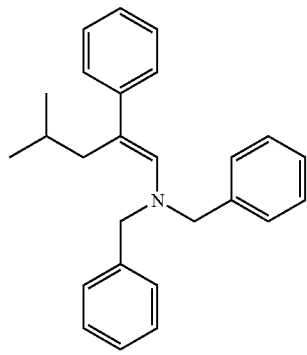
exemplified compound No. 28
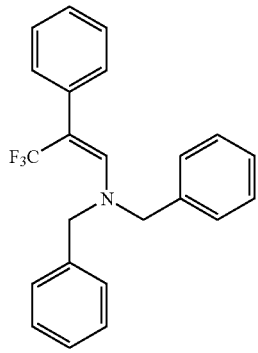
exemplified compound No. 29
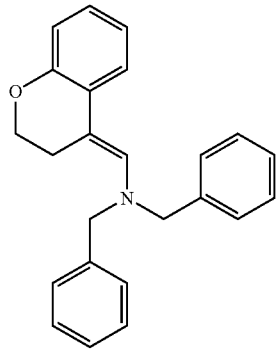

exemplified compound No. 30

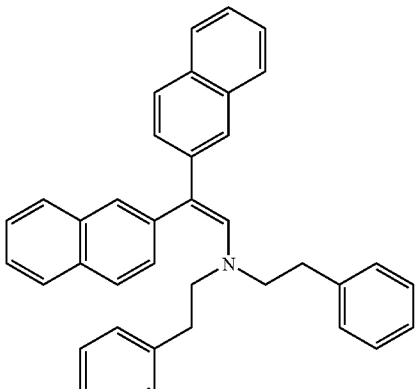

exemplified compound No. 31

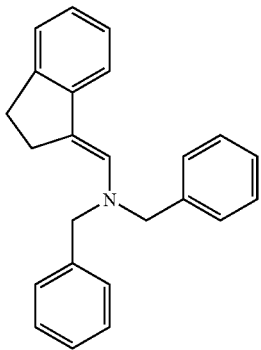

exemplified compound No. 32

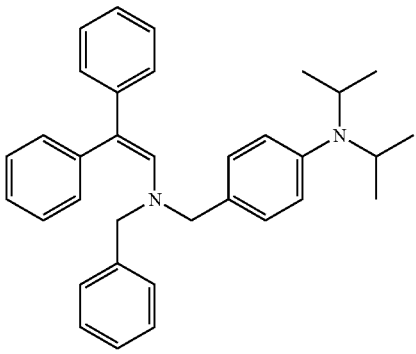

exemplified compound No. 33

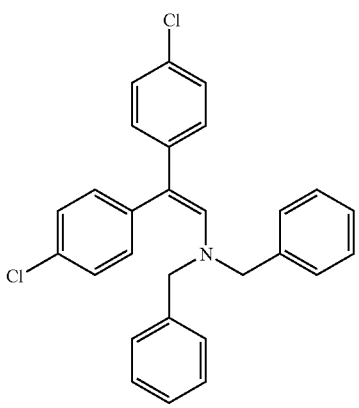

The enamine compound represented by the formula (1) according to the present invention can be produced in the following manner. When the enamine group E is (i), the target compound having high purity can be produced simply at high yield by a dehydration condensation reaction between an aldehyde compound represented by the formula (4) and a secondary amine compounds represented by the formula (5).

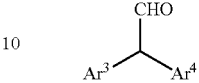
(4)

wherein $Ar^3$ and $Ar^4$ have the same meanings as those defined in the formula (1).

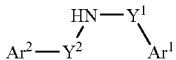
(5)

wherein $Ar^1$, $Ar^2$, $Y^1$ and $Y^2$ have the same meanings as those defined in the formula (1).

This dehydration condensation reaction may be run as follows.

An aldehyde compound represented by the formula (4) and an almost equimolar secondary amine compound represented by the formula (5) are dissolved in a solvent, to which an acid catalyst is added to react under heating. During the reaction, water is generated as a by-product and hinders the reaction and therefore, the produced water is removed out of the system together with a solvent by azeotropic distillation. After the reaction is completed, the precipitates are separated by filtration and are recrystallized from a single or mixed solvent system of ethanol, methanol and ethyl acetate, whereby the intended material having high purity can be obtained simply at high yield.

Any solvent may be used as the above solvent without any particular limitation insofar as it is inert to the above reaction and can dissolve or disperse the reaction substrates and the acid catalyst. Specific examples of the solvent include aromatic hydrocarbons such as toluene, xylene and chlorobenzene; ethers such as diethyl ether, tetrahydrofuran, ethylene glycol dimethyl ether, diethylene glycol dimethyl ether and 1,4-dioxane and alcohols such as butanol. These solvents may be used either singly or in combinations of two or more.

There is no particular limitation to the amount of the solvent to be used. It is preferable to design the amount appropriate to run the reaction smoothly corresponding to the reaction conditions such as the amount of the reaction substrate to be used, reaction temperature and reaction time.

Examples of the acid catalyst include p-toluenesulfonic acid, camphorsulfonic acid and pyridinium-p-toluenesulfonic acid.

The amount of the acid catalyst to be added is 1/10 to 1/1000 mol equivalent, preferably 1/25 to 1/500 mol equivalent and more preferably 1/50 to 1/200 mol equivalent based on 1 mol equivalent of the aldehyde compound represented by the formula (4).

The enamine compound represented by the formula (1) may be produced, for example, by using an aldehyde compound represented by the formula (4) and a secondary amine compound represented by the formula (5) as raw materials as shown by Production Examples 1 to 7 in Table 1.

The enamine compound according to the present invention is superior in ozone resistance. Therefore, a photoreceptor containing the enamine compound of the present invention in the photosensitive layer (particularly, a charge transport layer) has excellent electrophotographic characteristics, is resistant to the influence of ozone and nitrogen oxides generated from the system, provides stable characteristics and image quality even by repeated use and can attain extremely high durability.

Particularly, an enamine compound represented by the following structural formula is a novel compound.

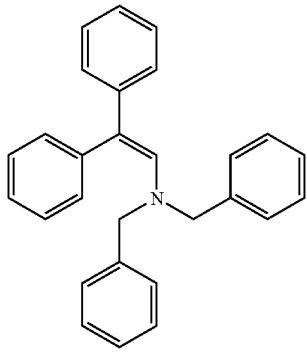

The enamine compound represented by the above structural formula may be produced by a dehydration condensation reaction between a dibenzylamine represented by the following structural formula:

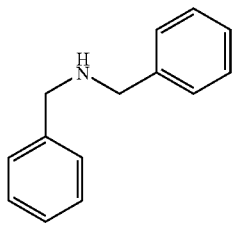

and a diphenylacetaldehyde represented by the following structural formula:

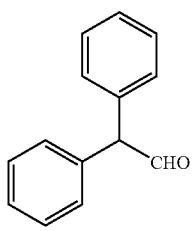

in the presence of an acid catalyst.

Next, the structure of the photoreceptor of the present invention will be explained.

FIGS. 1 to 8 are schematic cross-sectional views showing an essential part of the photoreceptor of the present invention.

FIGS. 1 to 4 are schematic cross-sectional views showing an essential part of a monolayer type photoreceptor with a monolayer type photosensitive layer constituted of one photosensitive layer.

Also, FIGS. 5 to 8 are schematic cross-sectional views showing an essential part of a laminate type photoreceptor (hereinafter referred to as "function separation type photoreceptor" as the case may be) with a laminate type photosensitive layer (hereinafter also referred to as "function separation type photosensitive layer") constituted of a charge generation layer and a charge transport layer. Although the photoreceptor of the present invention may be a reverse double layer type laminate structure in which the charge generation layer and the charge transport layer are formed in the reverse order, the above laminate type is preferable.

In the photoreceptor 11 of FIG. 1, a monolayer type photosensitive layer 2 is formed on the surface of a conductive support 1.

Figure 2:
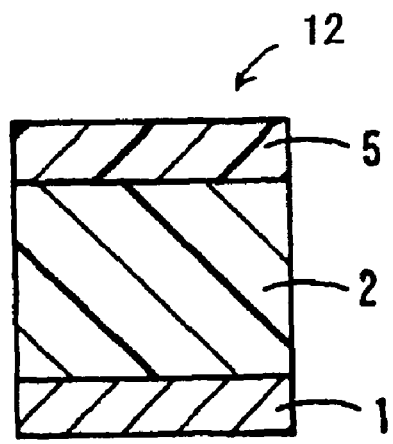
FIG. 2 is a schematic cross-sectional view showing the structure of an essential part of a monolayer type photoreceptor according to the present invention.

In the photoreceptor 12 of FIG. 2, a monolayer type photosensitive layer 2 and a surface protective layer 5 are formed in this order on a conductive support 1.

Figure 3:
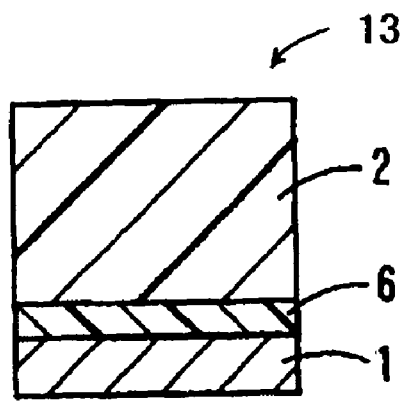
FIG. 3 is a schematic cross-sectional view showing the structure of an essential part of a monolayer type photoreceptor according to the present invention.

In the photoreceptor 13 of FIG. 3, an intermediate layer 6 and a monolayer type photosensitive layer 2 are formed in this order on a conductive support 1.

Figure 4:
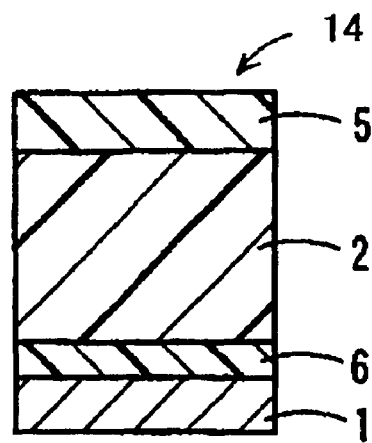
FIG. 4 is a schematic cross-sectional view showing the structure of an essential part of a monolayer type photoreceptor according to the present invention.

In the photoreceptor 14 of FIG. 4, an intermediate layer 6, a monolayer type photosensitive layer 2 and a surface protective layer 5 are formed in this order on a conductive support 1.

Figure 5:
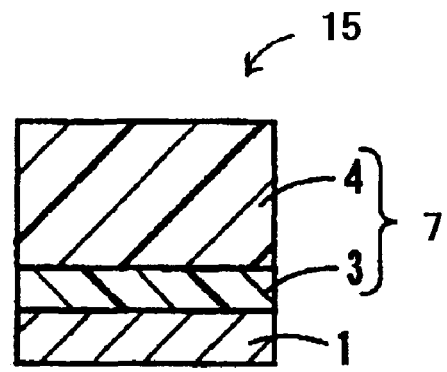
FIG. 5 is a schematic cross-sectional view showing the structure of an essential part of a laminate type photoreceptor according to the present invention.

In the photoreceptor 15 of FIG. 5, a laminate type photosensitive layer 7 prepared by laminating a charge generation layer 3 and a charge transport layer 4 in this order is formed on a conductive support 1.

Figure 6:
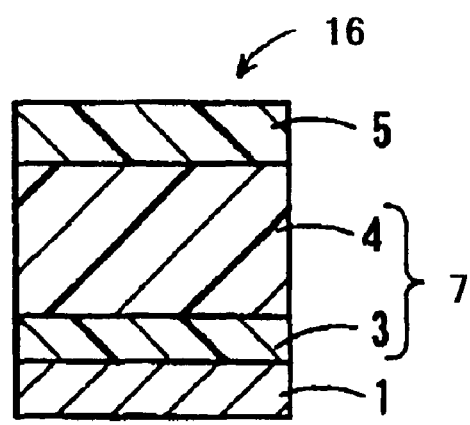
FIG. 6 is a schematic cross-sectional view showing the structure of an essential part of a laminate type photoreceptor according to the present invention.

In the photoreceptor 16 of FIG. 6, a laminate type photosensitive layer 7 prepared by laminating a charge generation layer 3 and a charge transport layer 4 in this order and a surface protective layer 5 are formed in this order on a conductive support 1.

Figure 7:
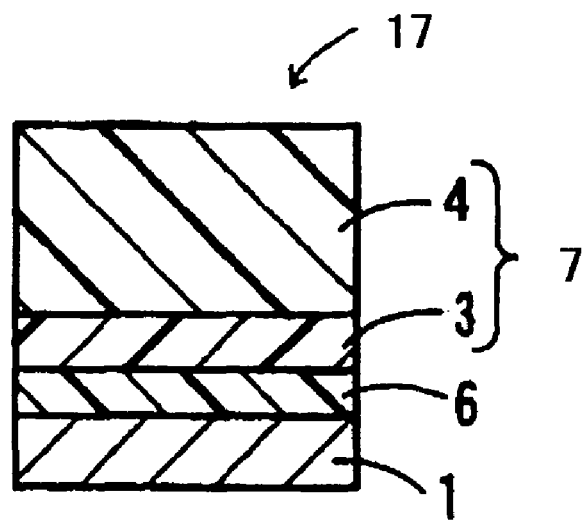
FIG. 7 is a schematic cross-sectional view showing the structure of an essential part of a laminate type photoreceptor according to the present invention.

In the photoreceptor 17 of FIG. 7, an intermediate layer 6 and a laminate type photosensitive layer 7 prepared by laminating a charge generation layer 3 and a charge transport layer 4 in this order are formed in this order on a conductive support 1.

Figure 8:
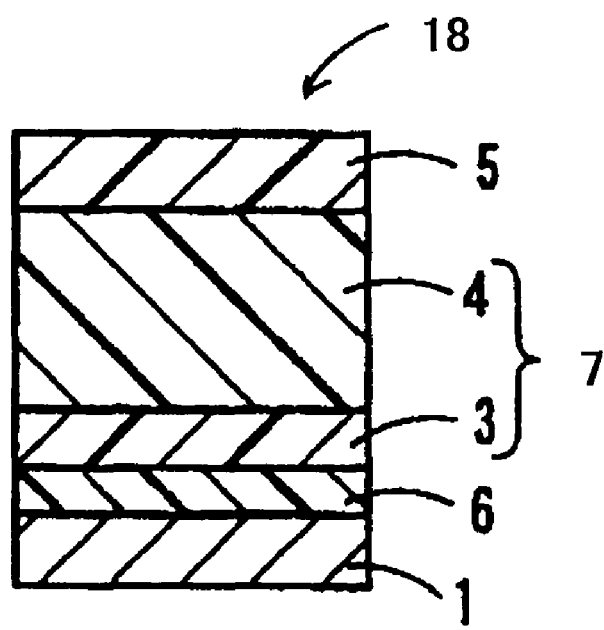
FIG. 8 is a schematic cross-sectional view showing the structure of an essential part of a laminate type photoreceptor according to the present invention.

In the photoreceptor 18 of FIG. 8, an intermediate layer 6, a laminate type photosensitive layer 7 prepared by laminating a charge generation layer 3 and a charge transport layer 4 in this order and a surface protective layer 5 are formed in this order on a conductive support 1.

(Conductive Support 1 (Photoreceptor Raw Tube))

No particular limitation is imposed on the structural material of the conductive support insofar as it is a material used in the fields concerned.

Specific examples of the structural material include metal materials such as aluminum, aluminum alloys, copper, zinc, stainless steel and titanium; polymer materials such as polyethylene terephthalate, polyamide, polyester, polyoxymethylene and polystyrene, and materials obtained by laminating a metal foil on, applying a metal material to or forming a layer of a conductive compound such as a conductive polymer, tin oxide and indium oxide by vapor deposition or application on the surface of a base material such as hard paper or glass.

The shape of the conductive support is not limited to a sheet form as shown in FIGS. 1 to 8 and may be a drum form, a column form or an endless belt form.

The surface of the conductive support 1 may be processed by anodic oxidation coating treatment, surface treatment using chemicals or hot water, coloring treatment or irregular reflection treatment such as surface roughing treatment according to the need to the extent that the image quality is not adversely affected.

The irregular reflection treatment is particularly effective when the photoreceptor of the present invention is used in an electrophotographic process using a laser as an exposure light source. Specifically, in the electrophotographic process using a laser as an exposure light source, the wavelengths of laser light are even. Therefore, there is the case where incident laser light interferes with the light reflected in the light-sensitive material, resulting in appearance of interference fringes on an image, causing image defects. In this respect, the above image defects caused by the interference of laser light having even wavelengths can be prevented by processing the surface of the conductive support by irregular reflection treatment.

(Monolayer Type Photosensitive Layer 2)

The monolayer type photosensitive layer contains a charge generation material, a charge transport material, the enamine compound of the present invention and a binder resin.

The charge generation material has the ability to absorb light, thereby generating charges.

As the charge generation material, compounds usually used in the fields concerned may be used.

Specific examples of materials effective for the charge generation material include organic pigments or dyes such as azo type pigments (for example, monoazo type pigments, bisazo type pigments and trisazo type pigments), indigo type pigments (for example, indigo and thioindigo), perylene type pigments (for example, perylene imide and perylenic acid anhydride), polycyclic quinone type pigments (for example, anthraquinone and pyrene quinone), phthalocyanine type pigments (for example, metal phthalocyanine and X-type nonmetal phthalocyanine), squalilium dyes, pyrylium salts and thiopyrylium salts, triphenylmethane type dyes and inorganic materials such as serene and amorphous silicon. These compounds may be either singly or in combinations of two or more.

Among these charge generation materials, phthalocyanine type pigments such as metal phthalocyanine and X-type nonmetal phthalocyanine are preferable and oxotitanium phthalocyanine particularly preferable.

The phthalocyanine type pigments have a high charge generation efficiency and charge injection efficiency, absorbs light to generate a large number of charges and can inject the generated charges into the charge transport material contained in the monolayer type photosensitive layer without accumulating them therein, with smoothly carrying the injected charges in the charge transport layer. Therefore, a photoreceptor having high sensitivity and high resolution can be obtained. The same effect is also obtained in a laminate type photoreceptor which will be described later.

Also, the charge generation material may be used in combination with sensitizing dyes.

Examples of these sensitizing dyes include triphenylmethane type dyes typified by Methyl Violet, Crystal Violet, Night Blue and Victoria Blue; acridine dyes typified by Erythrocin, Rhodamine B, Rhodamine 3R, Acridine Orange and Flapeocine; thiazine dyes typified by Methylene Blue and Methylene Green; oxazine dyes typified by Capri Blue and Meldola's Blue; cyanine dyes, styryl dyes, pyrylium salt dyes or thiopyrylium salt dyes.

The charge transport material has the ability to receive and transport the charges generated in the charge generation material and includes a hole transport material and an electron transport material.

As the hole transport material, compounds used in the fields concerned may be used.

Specific examples of the hole transport material include carbazole derivatives, pyrene derivatives, oxazole derivatives, oxadiazole derivatives, thiazole derivatives, thiadiazole derivatives, triazole derivatives, imidazole derivatives, imidazolone derivatives, imidazolidine derivatives, bisimidazolidine derivatives, stryl compounds, hydrazone compounds, polycyclic aromatic compounds, indole derivatives, pyrazoline derivatives, oxazolone derivatives, benzimidazole derivatives, quinazoline derivatives, benzofuran derivatives, acridine derivatives, phenazine derivatives, aminostilbene derivatives, triarylamine derivatives, triarylmethane derivatives, phenylenediamine derivatives, stilbene derivatives, enamine derivatives and benzidine derivatives, polymers having groups derived from these compounds on the principal chain or side chain (for example, poly-N-vinylcarbazole and poly-1-vinylpyrene, ethylcarbazole formaldehyde resins, triphenylmethane polymers and poly-9-vinylanthracene).

Also, as the electron transport material, compounds usually used in the fields concerned may be used.

Specific examples include benzoquinone derivatives, tetracyanoethylene derivatives, tetracyanoquinodimethane derivatives, fluorenone derivatives, xanthone derivatives, phenanthraquinone derivatives, phthalic acid anhydride derivatives and diphenoquinone derivatives. These charge transport materials may be used either singly or in combinations of two or more.

As the binder resin, resins which are used with the intention of improving the mechanical strength and durability of, for example, the monolayer type photosensitive layer and are used in the fields concerned may be used. The binder resin is preferably those which are highly compatible with the enamine compound of the present invention.

Specific examples of the binder resin include thermoplastic resins such as a polymethylmethacrylate, polystyrene, vinyl type resin such as a polyvinyl chloride, polycarbonate, polyester, polyester carbonate, polysulfone, polyarylate, polyamide, methacryl resin, acryl resin, polyether, polyacrylamide and polyphenylene oxide; thermosetting resins such as such as a phenoxy resin, epoxy resin, silicone resin, polyurethane, phenol resin, alkyd resin, melamine resin, phenoxy resin, polyvinylbutyral and polyvinylformal, partially crosslinked materials of these resins, copolymer resins containing two or more structural units contained in these resins (insulating resins such as a vinyl chloride/vinyl acetate copolymer resin, vinyl chloride/vinyl acetate/maleic acid anhydride copolymer resin and acrylonitrile/styrene copolymer resin). These binder resins may be used either singly or in combinations of two or more.

Among these resins, a polystyrene, polycarbonate, polyarylate and polyphenylene oxide are preferable because these materials are particularly highly compatible with the enamine compound of the present invention, have a volumetric resistance of $10^{13}$ Ω or more, so that they have high electric insulating characteristics and are also superior in film-forming ability and potential characteristics, and a polycarbonate is particularly preferably used.

The ratio of the charge transport material to the enamine compound of the present invention is as follows: when the amount of the charge transport material is A and the amount of the enamine compound is B, the ratio A/B is preferably 100/0.1 or more and 100/20 or less, though there is no particular limitation to the ratio.

When the amount of the enamine compound is less than 0.1 parts by weight or less based on 100 parts by weight of the charge transport material, there is the case where the enamine compound has a very small effect.

When the amount of the enamine compound of the present invention exceeds 20 parts by weight based on 100 parts by weight of the charge transport material, on the other hand, the ratio of the enamine compound to the charge transport material is high and there is the case of occurring the phenomenon such as deteriorating the sensitivity.

Also, the monolayer type photosensitive layer may also contain additives such as an antioxidant which are usually used in the fields concerned. Such additives improves the stability of a photosensitive layer forming coating solution to prolong the life of the solution and also, a photoreceptor produced using this coating solution is reduced in the content of oxidizing impurities, improving the durability of the photoreceptor, which is desirable.

Examples of the antioxidant include hindered phenol derivatives and hindered amine derivatives.

The ratio of the charge transport material to the antioxidant to be used is preferably 0.1 to 10 parts by weight based on 100 parts by weight of the charge transport material, though no particular limitation is imposed on the ratio. When the amount of the antioxidant to be used is less than 0.1 parts by weight, there is the case where the stability of the photosensitive layer forming coating solution which will be explained later and the effect of improving the durability of the photoreceptor are insufficient, whereas when the amount of the antioxidant exceeds 10 parts by weight, there is the case where the electric characteristics of the photoreceptor is adversely affected.

Though there is no particular limitation to the ratio of the binder resin to the enamine compound, charge generation material, charge transport material and additive added according to the need, the binder resin is preferably about 55 to 70% by weight based on the total amount.

When the ratio of the binder resin is less than 55% by weight, there is a fear that the film strength of the monolayer type photosensitive layer is decreased, whereas when the ratio exceeds 70% by weight on the contrary, there is a fear that the function of the monolayer type photosensitive layer is deteriorated. However, the ratio of the binder resin is designed to be less than 55% by weight when a surface protective layer is formed.

The monolayer type photosensitive layer 2 may be formed in the following manner. Specifically, the enamine compound of the present invention, the charge generation material, the charge transport material, the binder resin and additives such as an antioxidant according to the need are dissolved or dispersed in a proper solvent to prepare a photosensitive layer forming coating solution. Then, the coating solution is applied to the surface of the conductive support 1 or on the surface of the intermediate layer 6 formed on the conductive support 1. Then, the support is dried to remove the organic solvent and thus, the monolayer photosensitive layer can be formed. To describe in more detail, for example, the structural materials are dissolved or dispersed in a binder resin solution prepared by dissolving the binder resin in an organic solvent to prepare a monolayer type photosensitive layer forming coating solution.

Examples of the organic solvent include aromatic hydrocarbons such as benzene, toluene, xylene, mesitylene, tetralin, diphenylmethane, dimethoxybenzene and dichlorobenzene; hydrocarbon halides such as dichloromethane, dichloroethane and tetrachloropropane; ethers such as tetrahydrofuran (THF), dioxane, dibenzyl ether, dimethoxymethyl ether and 1,2-dimethoxyethane; ketones such as methyl ethyl ketone, cyclohexanone, acetophenone and isophrone; esters such as methyl benzoate, ethyl acetate and butyl acetate; sulfur-containing solvents such as diphenyl sulfide; fluorine type solvents such as hexafluoroisopropanol; and aprotic polar solvents such as N,N-dimethylformamide and N,N-dimethylacetamide. These compounds may be used either singly or in combinations of two or more. Also, mixed solvents obtained by adding alcohols, acetonitrile or methyl ethyl ketone to the above solvents may be used.

The charge generation material and other additives may be pre-milled prior to the process of dissolving or dispersing the structural materials in the resin solution.

The pre-milling may be carried out using a general milling machine, for example, a ball mill, sand mill, attritor, vibration mill or ultrasonic dispersing machine.

The dissolution or dispersion of the structural material in the resin solution may be carried out using a general dispersing machine such as a paint shaker, ball mill or sand mill. At this time, it is preferable to design proper dispersing conditions so as to prevent the occurrence of the phenomenon that impurities are generated by abrasion from the members constituting the container and dispersing machine and get mixed in the coating solution.

Examples of the method of applying the monolayer type photosensitive layer forming coating solution include roll coating, spray coating, blade coating, ring coating and dip coating.

The film thickness of the monolayer type photosensitive layer is preferably 5 to 100 µm and more preferably 10 to 50 µm though no particular limitation is imposed on the thickness. When the film thickness of the monolayer type photosensitive layer is less than 5 µm, there is a fear as to deterioration in charge retentivity of the surface of the photoreceptor, whereas when the film thickness of the monolayer type photosensitive layer exceeds 100 µm, there is a fear that the productivity of the photoreceptor is deteriorated.

(Laminate Type Photosensitive Layer 7)

The laminate type photosensitive layer is constituted of a charge generation layer 3 and a charge transport layer 4.

(Charge Generation Layer 3)

The charge generation layer 3 contains a charge generation material and a binder resin.

As the charge generation material, one or two or more types of the same charge generation materials that are contained in the monolayer type photosensitive layer may be used.

As the binder resin, one or two or more types of the same binder resins that are contained in the monolayer type photosensitive layer may be used.

Though there is no particular limitation to the ratio of the charge generation material to the binder resin to be used, the charge generation material is preferably contained in an amount of 10 to 99% by weight based on the total amount of the charge generation material and binder resin, which is balanced with the binder resin.

When the ratio of the charge generation material is less than 10% by weight, there is a fear as to a reduction in sensitivity, whereas when the ratio of the charge generation material exceeds 99% by weight, not only the film strength of the charge generation layer is reduced but also the dispersibility of the charge generation material is reduced with an increase in coarse particles, so that surface charges on the part other than the part to be eliminated by exposure are reduced and there is therefore a fear as to the occurrence of image defects and particularly many image fogs called black dot that is the phenomenon that toners are stuck to the white background to form fine black spots.

The charge generation layer may contain, according to the need, one or two or more types selected from a hole transport material, electron transport material, antioxidant, dispersion stabilizer and sensitizer in an appropriate amount besides the above two essential components. This improves the potential characteristics of the photoreceptor and also improves the stability of a charge generation layer forming coating solution which will be explained later, suppresses fatigue deterioration in the repeated use of the photoreceptor, making it possible to improve the durability of the photoreceptor.

A charge generation layer 3 may be formed by dissolving or dispersing the charge generation material, a binder resin and, according to the need, other additives in proper organic solvents to prepare a charge generation layer forming coating solution, by applying the coating solution to the surface of the conductive support 1 or to the surface of the intermediate layer 6 formed on the conductive support 1, and then the coating film is dried to remove solvents. To describes in more detail, the charge generation material and, according to the need, other additives are dissolved or dispersed in a resin solution prepared by dissolving the binder resin in an organic solvent to prepare a charge generation layer forming coating solution.

Other steps and other conditions conform to those in the formation of the monolayer type photosensitive layer.

As the organic solvent, one or two or more types of the same solvents that are used in the preparation of the monolayer type photosensitive layer forming coating solution may be used.

The film thickness of the charge generation layer 3 is preferably 0.05 to 5 μm and more preferably 0.1 to 1 μm though no particular limitation is imposed on the thickness. When the film thickness of the charge generation layer is less than 0.05 μm, the efficiency of light absorption is reduced and there is a fear as to a reduction in sensitivity, whereas when the film thickness of the charge generation layer exceeds 5 μm, the transport of charges in the charge generation layer is the rate determining step in the process of erasing charges on the surface of the photoreceptor and there is therefore a fear that the sensitivity is deteriorated.

(Charge Transport Layer 4)

The charge transport layer 4 contains a charge transport material, the enamine compound of the present invention and a binder resin.

As the enamine compound of the present invention, one or two or more types of the same enamine compounds that are contained in the monolayer type photosensitive layer may be used.

As the binder resin, one or two or more types of the same binder resins that are contained in the monolayer type photosensitive layer may be used.

The ratio of the charge transport material to the enamine compound of the present invention is the same as in the case of the monolayer type photosensitive layer.

The ratio of the charge transport material to the binder resin is the same as in the case of the monolayer type photosensitive layer.

The charge transport layer may contain the same additives such as an antioxidant contained in the monolayer type photosensitive layer according to the need besides the above three types of essential components.

A charge transport layer 4 may be formed by dissolving or dispersing the charge transport material, the enamine compound of the present invention, a binder resin and, according to the need, other additives in a proper organic solvent to prepare a charge transport layer forming coating solution, by applying the coating solution to the surface of the charge generation layer 3, and then the coating film is dried to remove the organic solvent. To describes in more detail, the charge transport material, the enamine compound of the present invention and, according to the need, other additives are dissolved or dispersed in a resin solution prepared by dissolving the binder resin in an organic solvent to prepare a charge transport layer forming coating solution.

Other steps and other conditions conform to those in the formation of the monolayer type photosensitive layer.

The film thickness of the charge transport layer 4 is preferably 5 to 50 μm and more preferably 10 to 40 μm though no particular limitation is imposed on the thickness. When the film thickness of the charge transport layer is less than 5 μm, there is a fear that the charge retentive ability of the surface of the photoreceptor is reduced, whereas when the film thickness of the charge transport layer exceeds 50 μm, there is a fear as to a reduction in the resolution of the photoreceptor.

(Surface Protective Layer)

The surface protective layer 5 has the ability to improve the durability of the photoreceptor and contains a charge transport material and a binder resin.

As the charge transport material, one or two or more types of the same charge transport materials that are contained in the monolayer type photosensitive layer may be used.

As the binder resin, one or two or more types of the same binder resins that are contained in the monolayer type photosensitive layer may be used.

A surface protective layer 5 may be formed by dissolving or dispersing the charge transport material, a binder resin and the like in a proper organic solvent to prepare a surface protective layer forming coating solution, by applying the coating solution to the surface of the monolayer type photosensitive layer 2 or to the surface of the laminate type photosensitive layer 7 and then the coating film is dried to remove the organic solvent. As the organic solvent to be used here, the same organic solvent that is used in the formation of the photosensitive layer 2 may be used.

Other steps and other conditions conform to those in the formation of the monolayer type photosensitive layer.

As the organic solvent, one or two or more types of the same solvents that are used in the preparation of the monolayer type photosensitive layer forming coating solution may be used.

The film thickness of the surface protective layer 5 is preferably 0.5 to 10 μm and more preferably 1 to 5 μm though no particular limitation is imposed on the thickness. When the film thickness of the surface protective layer 5 is less than 0.5 μm, there is a fear that the scratching resistance of the surface of the photoreceptor is deteriorated and there is therefore a fear as to inferior durability, whereas when the film thickness exceeds 10 μm, there is a fear that the resolution of the photoreceptor is reduced.

(Intermediate Layer 6)

The photoreceptor of the present invention is preferably provided with an intermediate layer between the conductive support and the monolayer type photosensitive layer or the laminate type photosensitive layer.

The intermediate layer has the ability to prevent the injection of charges into the monolayer type photosensitive layer or laminate type photosensitive layer from the conductive support. Specifically, the intermediate layer serves to suppress a reduction in the chargeability of the monolayer type photosensitive layer or laminate type photosensitive layer, to limit a reduction in surface charges on the part other than the part to be erased by exposure and to prevent the occurrence of image defects such as fogging. Particularly, the intermediate layer prevents the occurrence of image defects and particularly many image fogs called black dot which is the phenomenon that toners are stuck to the white background to form fine spots in the case of forming an image in the reverse developing process.

Also, the intermediate layer with which the surface of the conductive support is coated can reduce the degree of irregularities that are defects of the surface of the conductive support to uniform the surface, improve the film formation ability of the monolayer type photosensitive layer or laminate type photosensitive layer, and improve the adhesion (bonding ability) between the conductive support and the monolayer type photosensitive layer or laminate type photosensitive layer.

The intermediate layer may be formed, for example, by dissolving a resin material in an appropriate solvent to prepare an intermediate layer forming coating solution and by applying this coating solution to the surface of the conductive support, followed by drying to remove the organic solvent.

Examples of the resin material include natural macromolecular materials such as casein, gelatin, polyvinyl alcohol and ethyl cellulose, besides the same binder resins that are contained in the monolayer type photosensitive layer. These resin materials may be used either singly or in combinations of two or more.

Examples of the solvent used to dissolve or disperse the resin material include water, alcohols such as methanol, ethanol and butanol, grimes such as methyl carbitol and butyl carbitol and mixed solvents obtained by blending two or more of these solvents.

Other steps and other conditions conform to those in the formation of the monolayer type photosensitive layer.

Also, the intermediate layer forming coating solution may contain metal oxide particles.

The metal oxide particles ensure that the volume resistance of the intermediate layer can be regulated with ease, the injection of charges into the monolayer type photosensitive layer or laminate type photosensitive layer can be further suppressed and also, the electric characteristics of the photoreceptor can be maintained in various circumstances.

Examples of the metal oxide particles include titanium oxide, zinc oxide, aluminum oxide, aluminum hydroxide and tin oxide particles.

When the total content of the resin material and the metal oxide particles in the intermediate layer forming coating solution is C and the content of the solvent is D, the ratio by volume of (C/D) is preferably 1/99 to 40/60 (ratio by weight=0.01 to 0.67) and particularly preferably 2/98 to 30/70 (ratio by weight: 0.02 to 0.4).

Further, the ratio by volume (E/F) of the content (E) of the resin material to the content (F) of the metal oxide particles is preferably 1/99 to 90/10 (ratio by weight=0.01 to 9.0) and more preferably 5/95 to 70/30 (ratio by weight: 0.05 to 2.33).

The film thickness of the intermediate layer is, though not particularly limited to, preferably 0.01 to 20 µm and particularly preferably 0.1 to 10 µm. When the film thickness of the intermediate layer is less than 0.01 µm, the resulting intermediate layer does not substantially play its role and there is a fear that it fails to obtain a uniform surface which is formed by coating the surface therewith, whereas when the film thickness of the intermediate layer exceeds 20 µm, it is difficult to form a uniform intermediate layer and also, there is a fear that the sensitivity of the photoreceptor is deteriorated.

Note that when the structural material of the conductive support is aluminum, a layer containing alumite (alumite layer) may be formed as the intermediate layer.

An image formation apparatus according to the present invention is provided with the photoreceptor of the present invention, a charge means for charging the above photoreceptor, an exposure means for exposing the above charged photoreceptor with light and a developing means for developing the electrostatic latent image by exposure.

The image formation apparatus of the present invention will be explained with reference to the drawings. However, the image formation apparatus is not limited to the content of the following descriptions.

Figure 9:
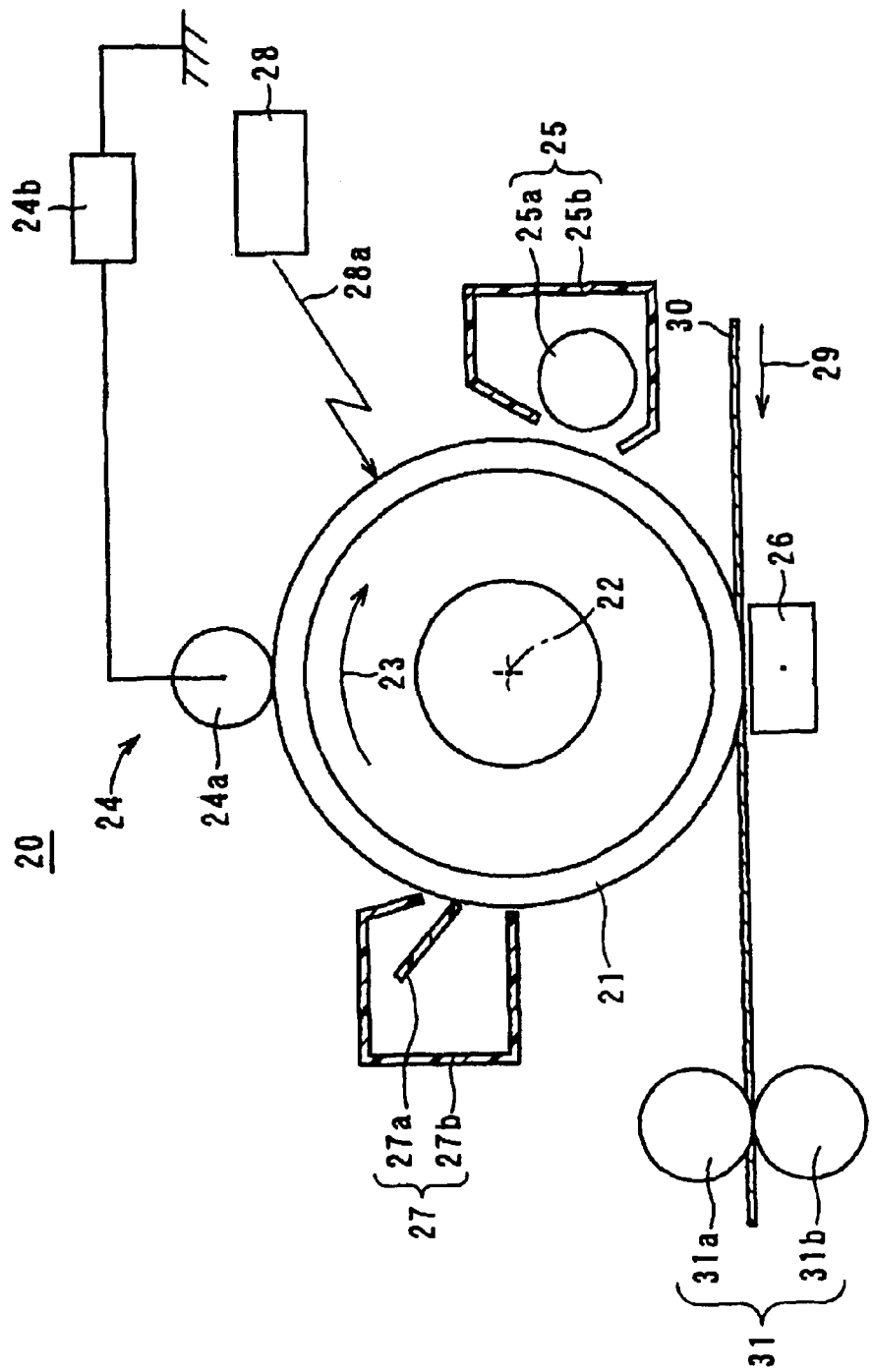
FIG. 9 is a schematic side view showing the structure of an image formation apparatus according to the present invention.

FIG. 9 is a schematic side view showing the structure of the image formation apparatus of the present invention.

An image formation apparatus 20 of FIG. 9 is provided with a photoreceptor 21 (for example, any one of the photoreceptors 11 to 18 shown in FIGS. 1 to 8) according to the present invention, a charge means (charger) 24, an exposure means 28, a developing means (developing unit) 25, a transfer device 26, a cleaner 27 and a fixing device 31. No. 30 in the figure indicates a transport paper.

The photoreceptor 21 is supported by the body of the image formation apparatus 20 (not shown) in a rotatable manner and is rotated in the direction of the arrow 23 around a rotation axis 22 by a driving means (not shown). The driving means has, for example, a structure including an electric motor and a reduction gear and transmits its driving force to the conductive support constituting the core body of the photoreceptor 21 to thereby rotate the photoreceptor 21 at a specified peripheral speed. The charger 24, the exposure means 28, the developing unit 25, the transfer device 26 and the cleaner 27 are disposed in this order towards the down stream side from the upstream side in the direction of the rotation of the photoreceptor 21 as shown by the arrow 23 along the outside periphery of the photoreceptor 21.

The charger 24 is a charge means for charging the outside periphery of the photoreceptor 21 to a specified potential. In this embodiment, the charger 24 is actualized by a structure constituted of a contact type charge roller 24a and a bias power source 24b applying voltage to the charge roller 24a.

Though a charge wire may also be used as the charge means, the photoreceptor formed with the surface protective layer according to the present invention produces a larger effect on the improvement of durability in a charge roller requiring of the surface of the photoreceptor high abrasive resistance.

Therefore, in the image formation apparatus of the present invention, the charge means is preferably a contact charge means.

The exposure means 28 is provided with, for example, a semiconductor laser as the light source and applies a light 28a such as a laser beam emitted from the light source, to the position between the charger 24 of the photoreceptor 21 and the developing unit 25 to expose the outside periphery of the charged photoreceptor 21 to light corresponding to image information. The photoreceptor 21 is scanned repeatedly by the light 28a in the major scanning direction parallel to the rotation axis 22 of the photoreceptor 21 and along with this scanning operation, an electrostatic latent image is gradually formed on the surface of the photoreceptor 21.

The developing unit 25 is a developing means for developing the electrostatic latent image formed on the surface of the photoreceptor 21 by exposure. The developing unit 25 is disposed facing the photoreceptor 21 and provided with a developing roller 25a that supplies a toner to the outside periphery of the photoreceptor 21 and a casing 25b that supports a developing roller 25a in such a manner as to be rotatable around the rotating axis parallel to the rotating axis 22 of the photoreceptor 21 and that stores a developer containing the toner in its inside space.

The transfer device 26 is a transfer means that transfers the toner image which is a visible image formed on the outside peripheral surface of the photoreceptor 21, to the transfer paper 30 which is a recording medium which is supplied between the photoreceptor 21 and the transfer device 26 from the direction of the arrow 29 by a conveying means (not shown). The transfer device 26 is, for example, a non-contact type transfer means that is provided with, for example, a charge means and provides charges having inverse polarity with respect to the toner to the transfer paper 30 to thereby transfer the toner image to the transfer paper 30.

The cleaner 27 is a cleaning means that removes and recovers the toner remaining on the outside peripheral surface of the photoreceptor 21 after the transfer operation using the transfer device 26. The cleaner 27 is provided with a cleaning blade 27a that peels the toner left on the outside peripheral surface of the photoreceptor 21 and a recovery casing 27b storing the toner peeled by the cleaning blade 27a. Also, this cleaner 27 is disposed together with a charge-removing lamp (not shown).

Also, the image formation apparatus 20 is provided with a fixing device 31 that is a fixing means that fixes the transferred image on the downstream side toward which the transfer paper 30 made to pass between the photoreceptor 21 and the transfer device 26 is conveyed. The fixing device 31 is provided with a heating roller 31a provided with a heating means (not shown) and a pressure roller 31b that is disposed facing the heating roller 31a and pressed by the heating roller 31a to form the contact part.

The image formation action of this image formation apparatus 20 is made as follows. First, when the photoreceptor 21 is rotated in the direction of the arrow 23 by a driving means, the surface of the photoreceptor 21 is positively or negatively charged uniformly to a prescribed potential by the charger 24 disposed on the upstream side of the image point of the light 28a of the exposure means 28 in the direction of the rotation of the photoreceptor 21.

Then, the surface of the photoreceptor 21 is irradiated with the light 28a emitted from the exposure means 28 corresponding to image information. In the photoreceptor 21, the surface charge on the parts irradiated with the light 28a is removed, which causes a difference in surface potential between the part irradiated with the light 28a and the part which is not irradiated with the light 28a, resulting in the formation of an electrostatic latent image.

The toner is supplied to the surface of the photoreceptor 21 from the developing unit 25 disposed on the downstream side of the image point of the light 28a of the exposure means 28 in the direction of the rotation of the photoreceptor 21, to develop the electrostatic latent image, thereby forming a toner image.

The transfer paper 30 is fed between the photoreceptor 21 and the transfer device 26 synchronously with the exposure for the photoreceptor 21. Charges having polarity opposite to that of the toner are provided to the fed transfer paper 30 to transfer the toner image formed on the surface of the photoreceptor 21 to the surface of the transfer paper 30.

The transfer paper 30 with the image transferred thereto is conveyed to the fixing device 31 by a conveying means, and heated and pressurized when it is made to pass through the contact part between the heating roller 31a and the pressure roller 31b to fix the toner image to the transfer paper 30, thereby forming a fast image. The transfer paper 30 on which an image is thus formed is discharged out of the image formation apparatus 20 by a conveying means.

On the other hand, the toner left on the surface of the photoreceptor 21 after the toner image is transferred by the transfer device 26 is peeled from the surface of the photoreceptor 21 by the cleaner 27 and recovered. The charges on the surface of the photoreceptor 21 from which the toner is removed in this manner is removed by light emitted from a charge-removing lamp, so that the electrostatic latent image on the surface of the photoreceptor disappears. Thereafter, the photoreceptor 21 is further rotated and then, a series of operations beginning with the charging operation are again repeated to form images continuously.

The image formation apparatus 20 according to the present invention is provided with the photoreceptor 21 having the photosensitive layer in which the enamine compound of the present invention is uniformly dispersed and therefore, a high quality image free from image defects such as black dots can be formed.

EXAMPLES

The present invention will be explained in detail by way of production examples, examples and comparative examples, however, the present invention is not limited to these production examples (except for comparison) and examples.

Note that the chemical structure, molecular weight and elemental analysis of each compound obtained in Production Examples were measured by the following devices and conditions.

(Chemical Structure)

Nuclear magnetic resonance device: NMR (Model: DPX-200, manufactured by Bulker Biospin k.k.)

Sample preparation about 4 mg sample/0.4 m (CDC13)

Measurement mode $^1$H (usual), $^{13}$C (usual, DPET-135)

(Molecular Weight)

Molecular weight measuring device: LC-MS (manufactured by Thermoquest K.K.), Finegan LCQ Deca Mass spectrometer system)

LC column GL-Science Intertsil ODS-3 2.1×100 mm

Column temperature 40° C.

Eluent Methanol:water=90:10

Amount of a sample to be injected 5 μl

Detector UV254 nm and MS ESI (Elemental Analysis)

Elemental analyzer: Elemental Analysis 2400, manufactured by Perkin Elmer Inc.

Amount of a sample: about 2 mg, exactly weighed

Flow amount of gas (ml/min): He=1.5, $O_2$=1.1, $N_2$=4.3

Combustion tube temperature setting: 925° C.

Reducing tube temperature setting: 640° C.

In this elemental analysis, the carbon (C)-hydrogen (H)-nitrogen (N) simultaneous quantitative method using the differential heat conductive method was used to analyze.

Production Example 1

1.97 g (1.0 equivalent) of dibenzylamine represented by the following structural formula (6) and 2.06 (1.05 equivalent) of diphenylacetaldehyde represented by the following structural formula (7) were added to 100 ml of toluene and 0.023 g (0.01 equivalent) of DL-10-camphorsulfonic acid was added as an acid catalyst to the above solution. The solution was heated on an oil bath at 120 to 140° C. with stirring to react the mixture for 6 hours while removing the by-produced water together with toluene by azeotropic distillation out of the system. After the reaction is finished, the resulting reaction solution was concentrated to a volume about 1/10 the original and added dropwise to 100 ml of hexane which was vigorously stirred, to produce crystals. The produced crystals were separated by filtration, washed with cooled ethanol and recrystallized from a mixture solvent of ethanol and ethyl acetate to obtain 3.04 g (yield: 81%) of a white powder compound.

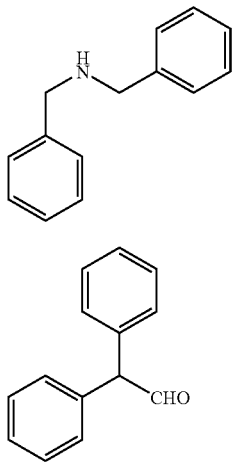

(6)

(7)

The obtained white powder compound was chemically analyzed to obtain the following results.

Nuclear magnetic resonance device: NMR (ppm)

$^1$H-NMR spectrum: δ=3.9 (S. 4H, benzyl CH$_2$), 6.7 (S. 1H, enamine CH), 7.2 to 7.8 (m. 20H benzene ring CH).

$^{13}$C-NMR spectrum: δ=56.1 (benzyl CH$_2$), 130.5 (enamine C), 132.9 (enamine CH), 125.3, 127.1, 127.6, 128.0, 128.4, 128.7, 128.9, 130.5 (benzene ring CH), 138.0, 138.4, 141.0 (benzene ring C).

Moreover, in the measurement using the molecular weight measuring device LC-MS, a peak corresponding to a molecular ion [M+H]$^+$ obtained by adding a proton to the exemplified compound No. 1 (molecular weight (calculated): 375.20) was observed at 376.2.

Further, the elemental analysis of the white powder compound was as follows.

<Elemental Analysis of the Exemplified Compound No. 1>

Theoretical value C, 89.56%, H, 6.71%, N, 3.73%

Actual value C, 89.35%, H, 6.95%, N, 3.70%

It was found from the above results of NMR, LC-MS, elemental analysis and the like that the obtained white powder compound is an enamine compound of the exemplified compound No. 1 (yield: 87.5%). Also, from the results of analysis of HPLC when the measurement using LC-MS was made, it was found that the purity of the exemplified compound (1) was 99.3%.

Production Examples 2 to 7

Synthesis of the exemplified compounds No. 2, 3, 7, 12, 17 and 24

The same procedures as in Production Example 1 were conducted using the raw material compounds shown in Table 1 as the amine compound and aldehyde compound to manufacture the exemplified compounds No. 2, 3, 7, 12, 17 and 24. In Table 1, the raw material compound used for the exemplified compound No. 1 is also shown.

TABLE 1

| Compound | Amine compound Formula (4) | Aldehyde compound Formula (5) |
| --- | --- | --- |
| Production Example 1 Exemplified compound No. 1 | | |
| Production Example 2 Exemplified compound No. 2 | | |
| Production Example 3 Exemplified compound No. 3 | | |

TABLE 1-continued

| Compound | Amine compound Formula (4) | Aldehyde compound Formula (5) |
|---|---|---|
| Production Example 4 Exemplified compound No. 7 | 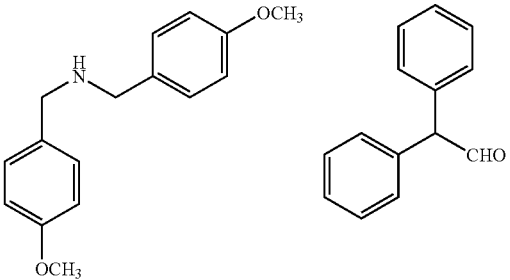 | 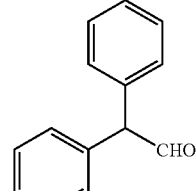 |
| Production Example 5 Exemplified compound No. 12 | 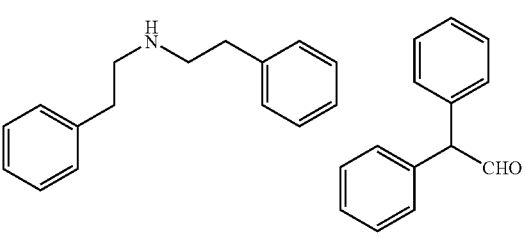 | 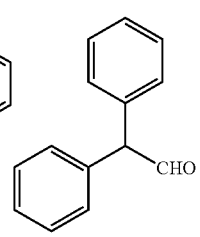 |
| Production Example 6 Exemplified compound No. 17 | 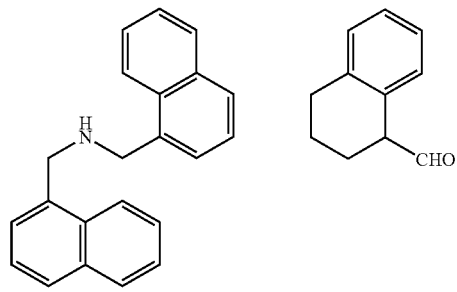 | 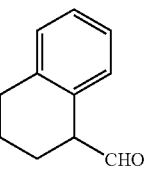 |
| Production Example 7 Exemplified compound No. 24 | 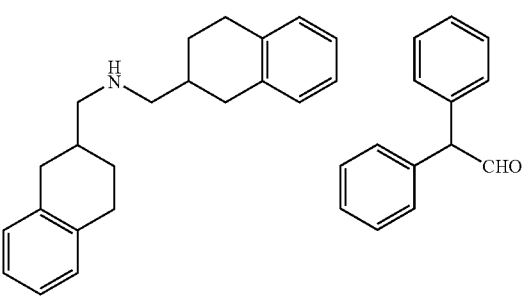 | 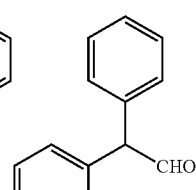 |

Also, the value of elemental analysis and calculated value and actual value [M+H] measured by LC-MS of the molecular weight of each of the exemplified compounds obtained in the above Production Examples 1 to 7 are shown in Tables 2-1 and 2-2.

TABLE 2-1

| Compound | Structural formula | Elemental analysis C (%) H (%) N (%) | LC-MS |
|---|---|---|---|
| Production Example 1 Exemplified compound No. 1 | 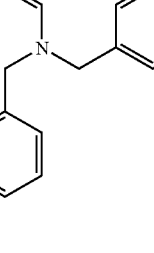 | Theoretical value 89.56  6.71  3.73 actual value 89.35  6.95  3.70 | Calculated value 375.2 actual value [M + H]+ 376.2 |
| Production Example 2 Exemplified compound No. 2 | 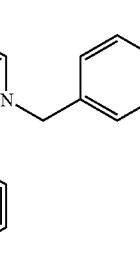 | Theoretical value 88.13  7.40  4.47 actual value 87.98  7.51  4.51 | Calculated value 313.2 actual value [M + H]+ 323.2 |
| Production Example 3 Exemplified compound No. 3 | 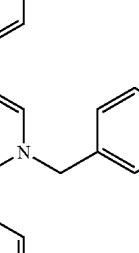 | Theoretical value 88.45  7.42  4.13 actual value 88.23  7.68  4.09 | Calculated value 339.2 actual value [M + H]+ 340.2 |
| Production Example 4 Exemplified compound No. 7 | 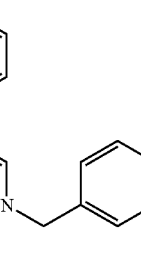 | Theoretical value 82.73  6.71  3.22 actual value 82.51  6.82  3.25 | Calculated value 435.2 actual value [M + H]+ 436.2 |

TABLE 2-2

| Compound | Structural formula | Elemental analysis C (%) H (%) N (%) | LC-MS |
|---|---|---|---|
| Production Example 5 Exemplified compound No. 12 | | Theoretical value 89.29  7.24  3.47 actual value 88.95  7.47  3.58 | Calculated value 403.2 actual value [M + H]+ 404.2 |
| Production Example 6 Exemplified compound No. 17 | | Theoretical value 90.16  6.65  3.19 actual value 89.85  6.89  3.26 | Calculated value 439.2 actual value [M + H]+ 440.2 |
| Production Example 7 Exemplified compound No. 24 | | Theoretical value 89.39  7.71  2.9 actual value 88.99  8.06  2.95 | Calculated value 483.3 actual value [M + H]+ 484.4 |

Example 1

A photoreceptor was produced in which the exemplified compound No. 1 which was the enamine compound produced in Production Example 1 according to the present invention was contained in the charge transport layer.

As the conductive support, a 100-μm thick polyethylene terephthalate (abbreviation: PET) film with aluminum deposited on the surface thereof (hereinafter referred to as "aluminum deposited PET film") was used.

7 parts by weight of titanium oxide (trade name: Tipaque TTO55A, manufactured by Ishihara Sangyo Kaisha, Ltd.) and 13 parts by weight of a copolymer nylon (trade name: Amilan CM8000, manufactured by Toray Industries, Inc.) were added in a mixed solution of 159 parts by weight of methyl alcohol and 106 parts by weight of 1,3-dioxoran. The mixture was subjected to dispersion treatment using a paint shaker for 8 hours to prepare 100 g of an intermediate layer forming coating solution. This intermediate layer forming coating solution was applied to the aluminum surface of an aluminum deposited PET film which was a conductive support by an applicator, followed by natural drying to form an intermediate layer having a film thickness of 1 μm.

Then, 1 part by weight of X-type nonmetal phthalocyanine (trade name: Fastogen Blue 8120, manufactured by Dainippon Ink and Chemicals, Incorporated) and 1 part by weight of butyral resin (trade name: #6000-C, manufactured by Denki kagaku Kogyo kabushiki Kaisha) were mixed in 98 parts by weight of methyl ethyl ketone and the mixture was subjected to dispersion treatment carried out by a paint shaker to prepare 50 g of a charge generation layer forming coating solution. This charge generation layer forming coating solution was applied to the surface of the intermediate layer formed previously in the same manner as in the case of the above intermediate layer and naturally dried to form a charge generation layer having a film thickness of 0.4 μm.

Then, 2.5 parts by weight of the enamine compound of the provided with an intermediate layer, a charge generation layer and a charge transport layer laminated in this order on a conductive support were manufactured in the same manner as in Example 1 except that the exemplified compounds 3, 12 and 24 were respectively used in place of the exemplified compound No. 1 which was the enamine compound according to the present invention.

Example 5

A laminate type photoreceptor having a laminate structure provided with an intermediate layer, a charge generation layer and a charge transport layer laminated in this order on a conductive support was manufactured in the same manner as in Example 1 except that a compound represented by the following structural formula (9) was used as the charge transport material.

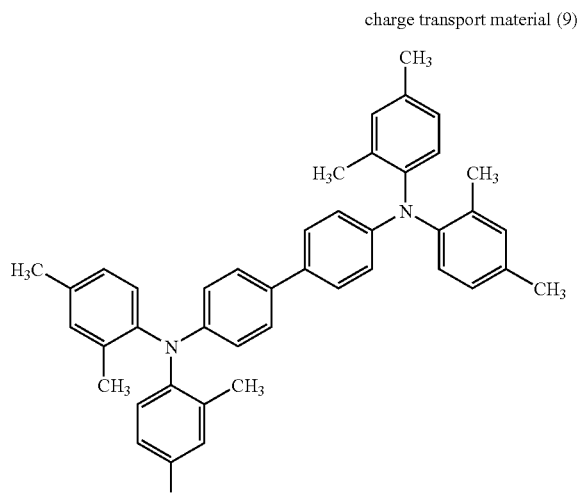

charge transport material (9)

Example 6 exemplified compound No. 1 produced in Production Example 1, 100 parts by weight of a charge transport material represented by the following structural formula (8) and 180 parts by weight of polycarbonate resin (trade name: Iupilon Z400, manufactured by Mitsubishi Gas Chemical Company, Inc.) were mixed with each other using toluene as a solvent to prepare 10 g of a charge transport layer forming coating solution having a solid content of 10% by weight. This charge transport layer forming coating solution was applied to the surface of the charge generation layer formed previously in the same manner as in the case of the intermediate layer to form two types of charge transport layers having different film thicknesses of 15 μm and 28 μm respectively. In this manner, a laminate type photoreceptor of the present invention was manufactured which had a laminate structure in which the intermediate layer, the charge generation layer and the charge transport layer are laminated in this order on the conductive support in the same manner as in the case of the photoreceptor 17 as shown in the foregoing FIG. 7.

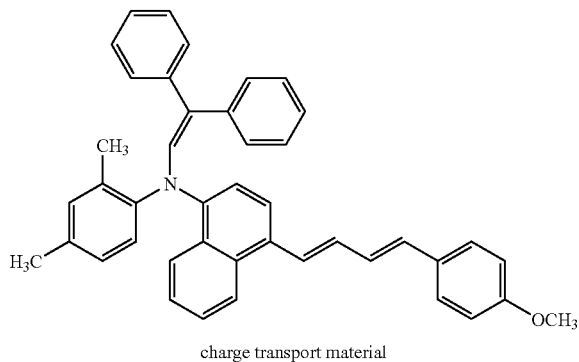

charge transport material

Examples 2 to 4

Laminate type photoreceptors having a laminate structure
A laminate type photoreceptor having a laminate structure provided with an intermediate layer, a charge generation layer and a charge transport layer laminated in this order on a conductive support was manufactured in the same manner as in Example 1 except that a compound represented by the following structural formula (10) was used as the charge transport material.

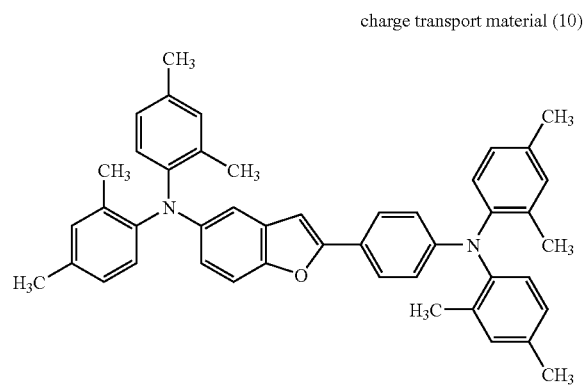

charge transport material (10)

Example 7

A laminate type photoreceptor having a laminate structure provided with an intermediate layer, a charge generation layer and a charge transport layer laminated in this order on a conductive support was manufactured in the same manner as in Example 1 except that 0.1 parts by weight of the enamine compound which was the exemplified compound No. 1 was used.

Example 8

A laminate type photoreceptor having a laminate structure provided with an intermediate layer, a charge generation layer and a charge transport layer laminated in this order on a conductive support were manufactured in the same manner as in Example 1 except that 20 parts by weight of the enamine compound which was the exemplified compound No. 1 was used.

Comparative Example 1

A laminate type photoreceptor was manufactured in the same manner as in Example 1 except the enamine compound of the present invention was not used.

Comparative Example 2

A laminate type photoreceptor was manufactured in the same manner as in Example 5 except the enamine compound of the present invention was not used.

Comparative Example 3

A laminate type photoreceptor was manufactured in the same manner as in Example 6 except the enamine compound of the present invention was not used.

Comparative Example 4

A laminate type photoreceptor was manufactured in the same manner as in Example 1 except that hydroxyethylbenzylamine (compound described in the publication of Japanese Unexamined Patent Publication No. HEI 3-172852) was used in place of the enamine compound of the present invention.

Comparative Example 5

A laminate type photoreceptor was manufactured in the same manner as in Example 1 except that a compound having the following structural formula (11) (compound described in the publication of Japanese Unexamined Patent Publication No. HEI 5-158258) was used in place of the enamine compound of the present invention.

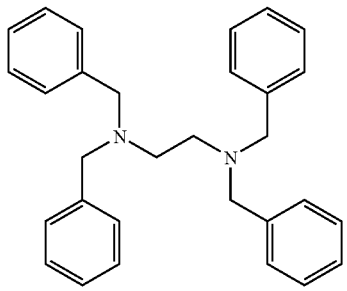

(11)

With regard to each photoreceptor obtained in Examples 1 to 8 and Comparative Examples 1 to 5 manufactured in the above manner, (a) ozone gas resistance and (b) stability of electric characteristics were evaluated in the following manner and (c) the overall rating of the performance of the photoreceptor was further made.

(a) Ozone Gas Resistance
(Evaluation by an Evaluating Apparatus)

Each photoreceptor for evaluation made in each evaluation apparatus (thickness of the charge transport layer: 15 μm) obtained in Examples 1 to 8 and Comparative Examples 1 to 5 was mounted on a test copying machine, to measure the surface potential $V_1$ (V) of the photoreceptor just after it was charged and the surface potential $V_2$ (V) of the photoreceptor three seconds after it was charged, in the N/N (Normal temperature/Normal humidity) circumstance of a temperature of 25° C. and a relative humidity of 50%. As the test copying machine, a copying machine was used which was provided with a surface potentiometer (trade name: CATE751, manufactured by Gentic Corporation) inside of a commercially available copying machine AR-F330 (trade name, manufactured by Sharp Kabushiki Kaisha) provided with a corona discharge/charge device as a photoreceptor charging means so that the surface potential of the photoreceptor in the course of image formation can be measured. The surface potential $V_1$ (V) of the photoreceptor just after it was charged and the surface potential $V_2$ (V) of the photoreceptor three seconds after it was charged were substituted in the following equation (I) to calculate charge retention rate DD (%) and this calculated value was defined as initial charge retention rate $DD_0$.

$$\text{Charge retention rate } DD(\%) = (V_2(V)/V_1(V)) \times 100 \qquad (1)$$

Then, an ozone generation/control apparatus (trade name: OES-10A, manufactured by Daylec Inc.) was used to expose each photoreceptor to ozone in a closed container in which the concentration of ozone was adjusted to about 7.5 ppm (confirmed by an ozone densitometer MODEL 1200 (trade name), manufactured by Daylec Inc.) for 20 hours. After exposed to ozone, the photoreceptor was allowed to stand in the normal temperature/normal humidity (N/N) circumstance of a temperature of 25° C. and a relative humidity of 50% for 2 hours and then, the charge retention rate DD (%) was calculated in the same manner as that before the photoreceptor was exposed to ozone and the obtained value was defined as charge retention rate $DD_{O2}$ after the photoreceptor was exposed to ozone.

The charge retention rate $DD_{O2}$ after the photoreceptor was exposed to ozone was subtracted from the charge retention rate $DD_0$ before the photoreceptor was exposed to ozone to obtain charge retention rate variation $\Delta DD$ (=$DD_0$-$DD_{O2}$) as the index of evaluation of ozone gas resistance.

(Evaluation Using an Actual Machine)

Each photoreceptor for evaluation made in an actual machine (thickness of the charge transport layer: 28 μm) obtained in Examples 1 to 8 and Comparative Examples 1 to 5 was mounted on a commercially available copying machine AR-F330 (trade name, manufactured by Sharp Kabushiki Kaisha) which was provided with a corona discharge/charge device as the charge means for the photoreceptor to actually print a test image having a given pattern on 50,000 recording sheets in the N/N (Normal temperature/Normal humidity) circumstance of a temperature of 25° C. and a relative humidity of 50%. After the actual printing of an image on 50,000 sheets was finished, the operation of the copying machine was suspended for 1 hour and then, a halftone image was copied on a recording sheet as a first evaluation image. Then, a test image having a given pattern was actually printed again on 50,000 recording sheets in the N/N (Normal temperature/Normal humidity) circumstance of a temperature of 25° C. and a relative humidity of 50%. After the actual printing of an image on 50,000 sheets was finished, the operation of the copying machine was suspended for 1 hour and then, a halftone image was copied on a recording sheet as a second evaluation image.

The formed first evaluation image and second evaluation image were respectively observed visually to rate the image quality of the part corresponding to the part of the recording sheet where the toner image was transferred from the part of the photoreceptor disposed close to the corona discharge/charger when the copying machine was suspended, based on the degree of generation of image defects such as white voids and black bands as the index of evaluation of ozone gas resistance. The standard of rating of image quality is as follows.

⊙: Excellent (No image defect occurs at all on both of the first and second evaluation images)

○: Good (Though slight image defects occur on one or both of the first and second evaluation images, these defects are negligible)

Δ: Acceptable (Though slight image defects occur on one or both of the first and second evaluation images, these defects are on practically unproblematic level)

x: Not acceptable (Many image defects occur on one or both of the first and second evaluation images, practical use is not allowed).

The above value of the charge retention rate variation ΔDD and the results of the rating of image quality were combined to evaluate the ozone resistance of the photoreceptor. The standard of evaluation of ozone gas resistance is as follows.

⊙Excellent (ΔDD is less than 3.0%, and the image quality is "Excellent (⊙)")

○: Good (ΔDD is 3.0% or more and less than 7.0%, and the image quality is "Excellent (⊙)", or ΔDD is less than 7.0%, and the image quality is "Good (○)")

Δ: No problem in practical use (ΔDD is less than 7.0%, and the image quality is "Acceptable (Δ)")

x: Inferior (ΔDD is 7.0% or more, and the image quality is "Not acceptable (x)").

(b) Stability of Electric Characteristics

Each photoreceptor for evaluation made in each actual machine (thickness of the charge transport layer: 28 μm) obtained in Examples 1 to 8 and Comparative Examples 1 to 5 was mounted on a test copying machine, to measure the stability of electric characteristics of the photoreceptor in the L/L (Low temperature/Low humidity) circumstance of a temperature of 5° C. and a relative humidity of 20% and in the H/H (High temperature/High humidity) circumstance of a temperature of 35° C. and a relative humidity of 85% in the following manner. As the test copying machine, a commercially available copying machine AR-F330 (trade name, manufactured by Sharp Kabushiki Kaisha) provided with a corona discharge/charge device as a photoreceptor charging means was used and provided with a surface potentiometer (trade name: CATE751, manufactured by Gentic Corporation) inside thereof so that the surface potential of the photoreceptor in the course of image formation can be measured. The copying machine AR-F330 is a negatively charged type image formation apparatus in which the surface of the photoreceptor is negatively charged to carry out the electrophotographic process.

Using a test copying machine mounted with each photoreceptor obtained in Examples 1 to 8 and Comparative Examples 1 to 5, the surface potential of the photoreceptor just after the charge operation was finished was measured as V0 (V) which was defined as initial charge potential $V0_1$. Also, the surface potential of the photoreceptor just after the exposure operation using laser light was finished was measured as Vr (V) which was defined as initial residual potential $Vr_1$.

Then, after a test image having a given pattern was continuously printed on 300,000 recording sheets, the charge potential V0 and the residual potential Vr were measured in the same manner as in the case of the initial measurement. The measured V0 and Vr were defined as the charge potential $V0_2$ after repeated use and the residual potential $Vr_2$ after repeated use respectively. The absolute value of the difference between the initial charge potential $V0_1$ and the charge potential $V0_2$ after repeated use was calculated as charge potential variation ΔV0 (=|$V0_1$-$V0_2$|). Also, the absolute value of the difference between the initial residual potential $Vr_1$ and the residual potential $Vr_2$ after repeated use was calculated as residual potential variation ΔVr (=|$Vr_1$-$Vr_2$|). The charge potential variation ΔV0 and residual potential variation ΔVr were used as the index of evaluation to evaluate the stability of electric characteristics.

The standard of evaluation of the stability of electric characteristics in the L/L circumstance is as follows:

⊙: Excellent (ΔV0 is 35 V or less and ΔVr is 55 V or less)

○: Good (ΔV0 is 35 V or less and ΔVr exceeds 55 V and 80 V or less, or ΔV0 exceeds 35 V and 75 V or less and ΔVr is 55 V or less)

Δ: No problem in practical use (ΔV0 exceeds 35 V and 75 V or less and ΔVr exceeds 55 V and 80 V or less)

x: Inferior (ΔV0 exceeds 75 V or ΔVr exceeds 80 V)

The standard of evaluation of the stability of electric characteristics in the H/H circumstance is as follows:

⊙: Excellent (ΔV0 is 15 V or less and ΔVr is 105 V or less)

○: Good (ΔV0 is 15 V or less and ΔVr exceeds 105 V and 125 V or less, or ΔV0 exceeds 15 V and 30 V or less and ΔVr is 105 V or less)

Δ: No problem in practical use (ΔV0 exceeds 15 V and 30 V or less and ΔVr exceeds 105 V and 125 V or less)

x: Inferior (ΔV0 exceeds 30 V or ΔVr exceeds 125 V)

Further, the results of evaluation in the L/L circumstance and the results of evaluation in the H/H circumstance were combined to make overall evaluation of the stability of electric characteristics. The standard of overall evaluation of the stability of electric characteristics is as follows.

⊙: Excellent ("Excellent (⊙)" both in the L/L circumstance and in the H/H circumstance)

○: Good ("Good (○)" in any one of the L/L circumstance and the H/H circumstance, and "Excellent (⊙)" or "Good (○)" in the other)

Δ: No problem in practical use ("No problem in practical use (Δ)" in any one of the L/L circumstance and the H/H circumstance, and not "Inferior (x)" in the other)

x: Inferior ("Inferior (x)" in any one or both of the L/L circumstance and the H/H circumstance).

(c) Overall Determination of Photoreceptor Performance

The results of evaluation of the ozone gas resistance and the results of the overall evaluation of the stability of electric characteristics were combined to make overall determination of photoreceptor performance. The standard of overall evaluation is as follows.

⊙: Excellent (Ozone gas resistance and the stability of electric characteristics are both "Excellent (⊙)")

○: Good (Any one of the ozone resistance and the stability of electric resistance is "Good (○)" and the other is "Excellent (⊙)" or "Good (○)")

Δ: No problem in practical use (Any one of the ozone resistance and the stability of electric resistance is "No problem in practical use (Δ)" and the other is not "Inferior (x)")

x: Inferior ("Inferior" in any one or both of the L/L circumstance and the H/H circumstance).

The above results of evaluation are shown in Table 3.

TABLE 3

| Example | Enamine compound Exemplified Compound No. | Enamine compound Amount (g) | Change Transport Material No. | Evaluation of Ozone Gas Resistance Initial Charge Retention Rate (DD) | Evaluation of Ozone Gas Resistance Charge Retention Rate Variation (Δ DD) | Image Quality | Evaluation |
|---|---|---|---|---|---|---|---|
| 1 | 1 | 2.5 | 8 | 90.8 | 2.8 | excellent | ⊚ |
| 2 | 3 | 2.5 | 8 | 90.8 | 3.1 | excellent | ⊚ |
| 3 | 12 | 2.5 | 8 | 91.5 | 2.9 | excellent | ⊚ |
| 4 | 24 | 2.5 | 8 | 90.2 | 2.5 | excellent | ⊚ |
| 5 | 1 | 2.5 | 9 | 91.1 | 2.6 | excellent | ⊚ |
| 6 | 1 | 2.5 | 10 | 90.8 | 2.9 | excellent | ⊚ |
| 7 | 1 | 0.1 | 8 | 90.2 | 3.5 | excellent | ⊚ |
| 8 | 1 | 20 | 8 | 92.5 | 2.1 | excellent | ⊚ |
| Co. Ex. 1 | — | — | 8 | 90.2 | 21.5 | not acceptable | X |
| Co. Ex. 2 | — | — | 9 | 91.8 | 22.6 | not acceptable | X |
| Co. Ex. 3 | — | — | 10 | 90.3 | 21.7 | not acceptable | X |
| Co. Ex. 4 | hydroxyethylbenzylamine (Japanese Unexaxmined Patent Publication No. HEI 3-172852) | 2.5 | 8 | 90.5 | 4.2 | acceptable | Δ |
| Co. Ex. 5 | structural formula (11) (Japanese Unexamined Patent Publication No. HEI 5-158258) | 2.5 | 8 | 90.1 | 3.7 | good | ○ |

| Example | Repeated Electric Properties L/L Electric Potential Properties Vo | L/L Δ Vo | L/L Δ Vr | L/L Evaluation | H/H Electric Potential Properties Vo | H/H Δ Vo | H/H Vr | H/H Δ Vr | H/H Evaluation | Overall Evaluation | Overall Determination |
|---|---|---|---|---|---|---|---|---|---|---|---|
| 1 | −672 | 29 | 40 | ⊚ | −664 | 15 | −30 | 65 | ⊚ | ⊚ | ⊚ |
| 2 | −675 | 33 | 42 | ⊚ | −665 | 13 | −31 | 70 | ⊚ | ⊚ | ⊚ |
| 3 | −671 | 32 | 39 | ⊚ | −659 | 15 | −29 | 65 | ⊚ | ⊚ | ⊚ |
| 4 | −668 | 29 | 37 | ⊚ | −655 | 18 | −30 | 68 | ⊚ | ⊚ | ⊚ |
| 5 | −679 | 25 | 39 | ⊚ | −668 | 19 | −30 | 69 | ⊚ | ⊚ | ⊚ |
| 6 | −672 | 28 | 39 | ⊚ | −662 | 18 | −31 | 68 | ⊚ | ⊚ | ⊚ |
| 7 | −670 | 33 | 42 | ⊚ | −655 | 25 | −39 | 72 | ⊚ | ⊚ | ⊚ |
| 8 | −680 | 25 | 35 | ⊚ | −665 | 16 | −29 | 68 | ⊚ | ⊚ | ⊚ |
| Co. Ex. 1 | −655 | 29 | 48 | ⊚ | −655 | 16 | −33 | 65 | ⊚ | ⊚ | X |
| Co. Ex. 2 | −683 | 30 | 42 | ⊚ | −649 | 17 | −31 | 67 | ⊚ | ⊚ | X |
| Co. Ex. 3 | −665 | 33 | 47 | ⊚ | −642 | 14 | −35 | 62 | ⊚ | ⊚ | X |
| Co. Ex. 4 | −648 | 41 | 53 | ○ | −645 | 9 | −43 | 110 | ○ | ○ | Δ |
| Co. Ex. 5 | −665 | 45 | 90 | X | −650 | 15 | −140 | 140 | X | X | X |

From a comparison between Examples 1 to 6 and Comparative Examples 1 to 3, it is understood that the photoreceptors of Examples 1 to 6 containing the enamine compound of the present invention are superior in ozone gas resistance and in the stability of electric characteristics to the photoreceptors of Comparative Examples 1 to 3, and exhibit good electric characteristics even in repeated use.

Also, it is understood that the photoreceptors according to the present invention exhibit the same performance when charge transport materials having various skeletons are used and therefore, have a wide range of applications for various charge transport materials.

Moreover, it is understood from the results of Examples 7 and 8 that when the amount of the enamine compound of the present invention to be added is in a range from 0.1 to 20 parts by weight based on 100 parts by weight of the charge transport material, good effects are produced.

From a comparison between Example 1 and Comparative Example 4 or 5, it is found that known amine type or diamine type materials are clearly different from the enamine compound of the present invention in the evaluation of various qualities extending image qualities and the photoreceptor of Example 1 using the enamine compound of the present invention is superior to photoreceptors using these amine type or diamine type materials.

As mentioned above, containing the enamine compound represented by the general formula (1) enables to obtain a photoreceptor excellent in electric characteristics such as charging ability and responsive ability, also in ozone resistance and in characteristic stability, that is, in resistance to a reduction in the above electric characteristics even in repeated use.

What is claimed is:

1. An electrophotographic photoreceptor comprising laminating a monolayer type photosensitive layer containing a charge generation material and a charge transport material or a laminate type photosensitive layer obtained by laminating a charge generation layer containing a charge generation material and a charge transport layer containing a charge transport material in this order, on a conductive support, wherein the charge transport layer of the monolayer type photosensitive layer or laminate type photosensitive layer contains an enamine compound represented by the following formula (1):

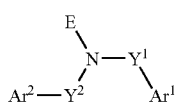
(1)

wherein $Ar^1$ and $Ar^2$, which may be the same or different, respectively represent an aryl group which may have a substituent, a cycloalkyl group which may have a substituent or a monovalent heterocyclic residue which may have a substituent;
$Y^1$ and $Y^2$, which may be the same or different, represent a straight or branched chain alkylene group which may have a substituent;
E represents an enamine group selected from the following formulae (i), (ii) and (iii):

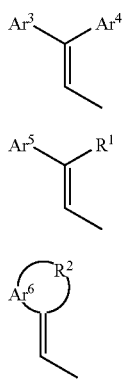
(i)

(ii)

(iii)

wherein $Ar^3$, $Ar^4$, $Ar^5$ and $Ar^6$, which may be the same or different, respectively represent an aryl group which may have a substituent; $R^1$ represents an alkyl group which may have a substituent; $R^2$ represents a straight or branched chain alkylene group which may have a substituent, an oxygen atom or a sulfur atom.

2. The electrophotographic photoreceptor of claim 1, wherein the enamine compound is represented by sub-formula (2):

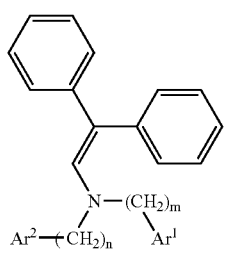
(2)

wherein $Ar^1$ and $Ar^2$ are the same as those defined in the formula (1); and n and m, which may be the same or different, respectively denote an integer from 1 to 3.

3. The electrophotographic photoreceptor of claim 1, wherein the enamine compound is represented by sub-formula (3):

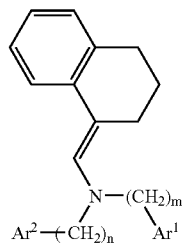
(3)

wherein $Ar^1$ and $Ar^2$ are the same as those defined in the formula (1); and n and m, which may be the same or different, respectively denote an integer from 1 to 3.

4. The electrophotographic photoreceptor of claim 1, wherein the enamine compound is selected from the following compounds

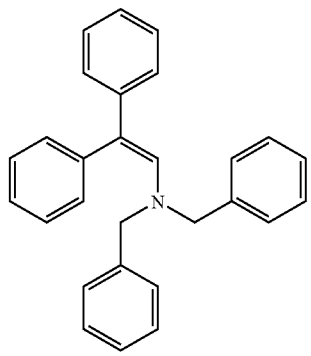

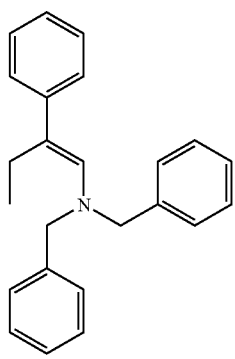

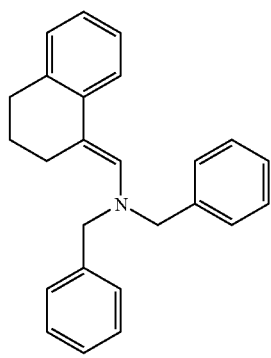

-continued

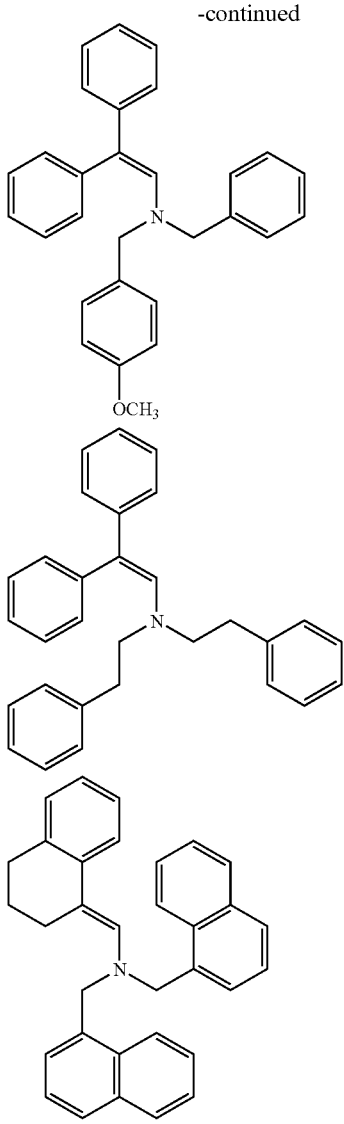

-continued

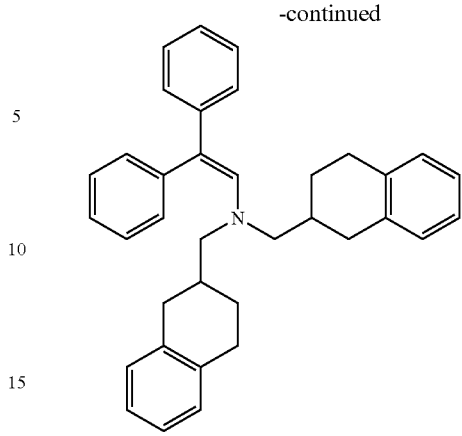

5. The electrophotographic photoreceptor of claim 1, wherein the ratio A/B (by weight) of the charge transport material A and the enamine compound B is 100/0.1 or more and 100/20 or less.

6. The electrophotographic photoreceptor of claim 1, wherein an intermediate layer is provided between the conductive support and the monolayer type photosensitive layer or the laminate type photosensitive layer.

7. An image formation apparatus comprising the electrophotographic photoreceptor of claim 1, a charge means for charging the electrophotographic photoreceptor, an exposure means for exposing the charged electrophotographic photoreceptor to light and a developing means for developing the electrostatic latent image formed by the exposure.

8. An image formation apparatus of claim 7, wherein the charge means is a contact charge means.

* * * * *